United States Patent [19]

Hoey et al.

[11] 4,314,055
[45] Feb. 2, 1982

[54] 3,5-DISUBSTITUTED-2,4,6-TRIIODOANILIDES OF POLYHYDROXY-MONOBASIC ACIDS

[75] Inventors: George B. Hoey, Ferguson; George P. Murphy, Creve Coeur, both of Mo.; Philip E. Wiegert, Glens Falls, N.Y.; James W. Woods, Creve Coeur, Mo.

[73] Assignee: Mallinckrodt, Inc., St. Louis, Mo.

[21] Appl. No.: 782,421

[22] Filed: Mar. 29, 1977

Related U.S. Application Data

[63] Continuation-in-part of Ser. No. 617,081, Sep. 29, 1975, abandoned, which is a continuation-in-part of Ser. No. 519,115, Oct. 30, 1974, abandoned.

[51] Int. Cl.$^3$ .................. A61K 49/04; C07H 3/00; C07C 103/78
[52] U.S. Cl. .................. 536/53; 260/340.7; 260/340.9 R; 260/345.7 R; 424/5; 564/50; 564/82; 564/99; 564/153; 564/158
[58] Field of Search .......... 260/559 A, 562 R, 578 A, 260/553 A, 556 A, 345.7, 340.7, 340.9 R; 424/5; 564/153, 158, 82, 99, 50; 536/53

[56] References Cited

U.S. PATENT DOCUMENTS 2,921,884 1/1960 Nachod et al. ............. 260/211 R X
3,082,202 3/1963 Madsen et al. ................. 260/211 R
3,144,479 8/1964 Obendorf .................. 260/211 R X
3,145,197 8/1964 Hoey ................... 260/211 R
3,446,837 5/1969 Wallingford ............... 260/562 R X
3,553,259 1/1971 Felder et al. ............... 260/558 A X
3,637,824 1/1972 Holtermann et al. .......... 260/518 A
3,661,975 5/1972 Korver ...................... 260/518 A X
3,666,799 5/1972 Bernstein et al. ............. 260/518 A
3,701,771 10/1972 Almen et al. ................. 260/211 R
3,953,501 4/1976 Klieger et al. ................ 424/5 X
4,001,323 1/1977 Felder et al. ................. 424/5
4,224,440 9/1980 Smith ......................... 536/53
4,230,845 10/1980 Smith ......................... 536/53 X
4,256,729 3/1981 Lin ........................... 424/5

OTHER PUBLICATIONS

Soulal et al., CA 80:120582q (1974).
Obendorf et al., CA 80:108545x (1974).

Primary Examiner—Thomas A. Waltz
Attorney, Agent, or Firm—Senniger, Powers, Leavitt and Roedel

[57] ABSTRACT

Certain 3,5-disubstituted-2,4,6-triiodoanilides of polyhydroxy-monobasic acids are useful as x-ray contrast agents. Representative of this class of compounds is the compound 3-gluconamido-2,4,6-triiodo-N-methyl-5-(N-methyl-acetamido)-benzamide and the compound 3-gluconamido-5-[N-(2-hydroxyethyl)acetamido]-2,4,6-triiodo-N-methylbenzamide.

18 Claims, No Drawings

3,5-DISUBSTITUTED-2,4,6-TRIIODOANILIDES OF POLYHYDROXY-MONOBASIC ACIDS

CROSS-REFERENCE TO RELATED APPLICATION

This application is a continuation-in-part of our application Ser. No. 617,081, filed Sept. 29, 1975 which in turn is a continuation-in-part of our application Ser. No. 519,115, filed Oct. 30, 1974, both now abandoned.

BACKGROUND OF THE INVENTION

This invention relates to the field of organic chemistry, and more particularly to novel 3,5-disubstituted-2,4,6-triiodoanilides of polyhydroxy-monobasic acids useful as non-ionic x-ray contrast media.

As is known, many 2,4,6-triiodobenzoic acid derivatives have been proposed and used as x-ray contrast agents. In general, it has been the practice to convert these compounds to salts, such as for example, the sodium and N-methylglucamine salts in order to render the compounds water-soluble and suitable for intravenous administration.

More recently, Almen et al. (U.S. Pat. No. 3,701,771, dated Oct. 31, 1972) have disclosed certain non-ionic N-(2,4,6-triiodobenzoyl)-sugar amines which are stated to be useful as x-ray contrast agents in the cerebrospinal cavities. In these compounds, a polyhydroxyalkyl chain is coupled to an iodoaromatic moiety in order to impart water solubility without resorting to ionic species. Certain of the non-ionic compounds disclosed in this patent were reported to be highly soluble in water while others were reported to have a medium or low water solubility.

In certain instances, non-ionic x-ray contrast media have been found to be less toxic than their ionic counterparts. This is believed to be due at least in part to the fact that the non-ionic compounds, being substantially non-ionized in aqueous solution, create less of an osmotic imbalance than do ionic compounds, i.e., non-ionic x-ray contrast media contribute only one molecular species per iodinated moiety as compared to ionic x-ray contrast media which contribute two or more species per iodinated moiety.

An interest has developed, therefore, in the synthesis of water-soluble, non-ionic x-ray contrast media possessing low toxicity and high iodine content for use in the x-ray visualization of areas of the body such as, for example, the cardiovascular system where high concentrations of contrast media are required in order to provide sufficient opacity.

SUMMARY OF THE INVENTION

Among the several objects of the invention may be mentioned the provision of novel, 3,5-disubstituted-2,4,6-triiodoanilides of polyhydroxy-monobasic acids; the provision of such compounds which are useful for the preparation of non-ionic x-ray contrast media; the provision of certain novel intermediates which are useful in the preparation of such compounds; and the provision of methods of preparing such compounds. Other objects and features will be in part apparent and in part pointed out hereinafter.

The present invention is thus directed to compounds of the formula:

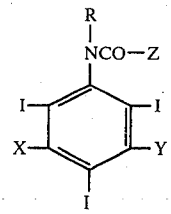

wherein X and Y are each non-ionizing functions compatible with water solubility and/or low toxicity in the 2,4,6-triiodophenyl configuration, R is selected from the group consisting of hydrogen, lower alkyl, hydroxy-lower alkyl and polyhydroxy-lower alkyl and CO-Z is the acyl residue of a polyhydroxy-monobasic acid, said acyl residue containing not more than 8 carbon atoms in its chain or ring.

The invention is further directed to intermediate compounds of the formula:

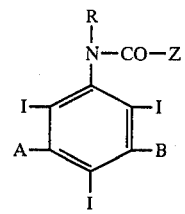

wherein CO—Z is selected from the group consisting of ester, acetal and ketal derivatives of an acyl residue of a polyhydroxy-monobasic acid, said acyl residue containing not more than 8 carbon atoms in its chain or ring, each of A and B is a non-hydroxyl-containing, non-ionizing function compatible with water solubility and/or low toxicity in the 2,4,6-triiodophenyl configuration or is a derivative of an hydroxyl-containing, non-ionizing function compatible with water solubility and/or low toxicity in the 2,4,6-triiodophenyl configuration, in which derivative the hydroxyl groups have been converted to O—CO—Z groups and R is hydrogen or lower alkyl or is a derivative of an hydroxy (lower alkyl) group in which the hydroxyl groups have been converted to O—CO—Z groups.

In a preferred embodiment of the invention, the intermediate compounds have the formula:

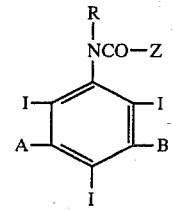

wherein B is a non-ionizing function compatible with water solubility and/or low toxicity in the 2,4,6-triiodophenyl configuration, CO-Z is selected from the group consisting of ester, acetal and ketal derivatives of an acyl residue of a polyhydroxy-monobasic acid, said acyl residue containing not more than 8 carbon atoms in its chain or ring, A is a derivative of an N-[hydroxy-(lower alkyl)] lower acylamino group in which the hydroxyl groups have been converted to O—CO—Z groups and R is hydrogen or lower alkyl or is a derivative of an hydroxy(lower alkyl) group in which the hydroxyl groups have been converted to O—CO—Z groups.

The invention also includes the step in a method of preparing compounds of the formula:

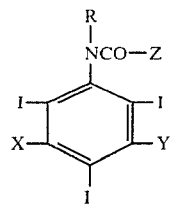

wherein X and Y are each non-ionizing functions compatible with water solubility and/or low toxicity in the 2,4,6-triiodophenyl configuration, R is selected from the group consisting of hydrogen, lower alkyl and hydroxy-lower alkyl and CO—Z is the acyl residue of a polyhydroxymonobasic acid, said acyl residue containing not more than 8 carbon atoms in its chain or ring, which comprises reacting a compound of the formula:

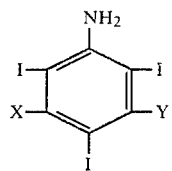

where X and Y are as defined above, with a compound of the formula

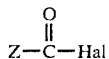

wherein Hal is selected from the group consisting of chlorine and bromine and Z—CO is selected from the group consisting of ester, acetal and ketal derivatives of an acyl residue of a polyhydroxymonobasic acid.

DESCRIPTION OF THE PREFERRED EMBODIMENTS

In accordance with the invention, it has been found that certain novel compounds of the following structure are useful as non-ionic x-ray contrast agents:

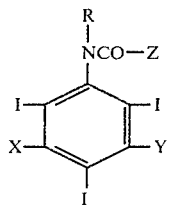

wherein X and Y are each non-ionizing functions compatible with water solubility and/or low toxicity in the 2,4,6-triiodophenyl configuration, R is selected from the group consisting of hydrogen, lower alkyl and hydroxy-lower alkyl and CO—Z is the acyl residue of a polyhydroxymonobasic acid, the acyl residue containing not more than 8 carbon atoms in its chain or ring.

Preferably, CO—Z is the acyl residue of a polyhydroxy-monobasic acid from the group consisting of aldonic acids, branched chain polyhydroxy-alkanoic acids, uronic acids, deoxy-aldonic acids, acylamino-deoxy-aldonic acids, and polyhydroxy-cycloalkane carboxylic acids. The aldonic acids are those of the formula:

where n=1 to 6 and include acids such as gluconic acid, gulonic acid, mannonic acid, galactonic acid, talonic acid, xylonic acid, glyceric acid and various other trionic, tetronic, pentonic, hexonic, heptonic and octonic acids. Various branched chain polyhydroxy-alkanoic acids may be employed as the source of the acyl residue CO—Z. Representative acids of this type include those of the following formulae:

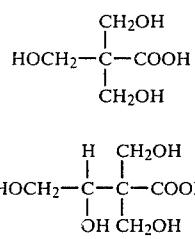

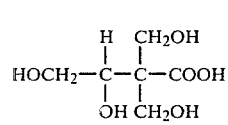

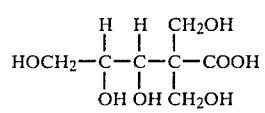

Uronic acids of the formula:

where n=1 to 6 may be employed as the source of the acyl residue. Representative uronic acids include galacturonic acid, glucuronic acid, gulluronic acid, and various other penturonic, hexuronic, hepturonic and octuronic acids. The term "uronic acids" as used herein also include such acids in cyclized form.

The deoxy-aldonic acids used as the source of the acyl residue include the 2-deoxy-aldonic acids of the formula:

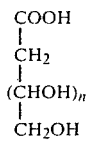

wherein n=1 to 5 and the corresponding 3-deoxy-aldonic acids, 4-deoxy-aldonic acids, etc. Other deoxy-aldonic acids included are the 2-deoxy-2-oxoaldonic acids of the formula:

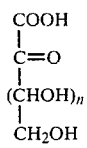

wherein n=1 to 5 and the corresponding 3-deoxy-3-oxoaldonic acids, 4-deoxy-4-oxoaldonic acids, etc. Among such deoxy-aldonic acids may be mentioned 2-deoxy-2-oxogluconic acid, 3-deoxy-gulonic acid, 4-deoxy-4-oxo-galactonic acid, etc.

The acylamino-deoxy-aldonic acids include the 2-acylamino-2-deoxy-aldonic acids of the formula:

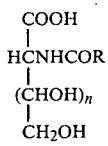

wherein n=1 to 5 and R is lower alkyl or hydroxy-(lower alkyl) and the corresponding 3-acylamino-3-deoxy-aldonic acids, 4-acylamino-4-deoxy-aldonic acids, etc. Representative acids of this type include 3-acetylamino-3-deoxygluconic acid, 2-propionylamino-2-deoxy-galactonic acid, 2-acetylamino-2-deoxy-gulonic acid, etc.

As polyhydroxy-cycloalkane carboxylic acids which may be employed as the source of the acyl residue CO—Z, there may be mentioned pentahydroxy-cyclohexane carboxylic acids, tetrahydroxy-cyclopentane carboxylic acids, 2,4,6-trihydroxy-cyclohexane carboxylic acids and hexahydroxy-cycloheptane carboxylic acids.

The acyl residue CO—Z should contain not more than 8 carbon atoms and preferably 6 or 7 carbon atoms, and as indicated, may be in the form of a chain or ring.

As mentioned, R may be hydrogen, lower alkyl such as methyl, ethyl or propyl, hydroxy-lower alkyl such as 2-hydroxyethyl, hydroxypropyl, dihydroxypropyl, or tris(hydroxymethyl)methyl. As used herein, the term hydroxy-lower alkyl encompasses monohydroxyalkyl and polyhydroxyalkyl groups.

The substituents in the 3- and 5-positions of the ring, namely X and Y, are non-ionizing functions compatible with water solubility and/or low toxicity in the 2,4,6-triiodophenyl configuration. As is known by those skilled in the art, the term "detoxifying and/or solubilizing groups" has been used as a generic designation for a substantial number of functional groups whose occurrence in the meta-position in a 2,4,6-triiodobenzoic acid has come to be associated with compounds which exhibit a relatively low toxicity and/or a relatively high water solubility (cf. G. B. Hoey, P. E. Wiegert and R. D. Rands, Jr., "Organic Iodine Compounds as X-Ray Contrast Media", in *International Encyclopedia of Pharmacology and Therapeutics* Section 76, "Radiocontrast Agents", P. K. Knoefel, Section Editor; Pergamon Press; Vol. 1, pp. 23-40, 54-73 (1971)). While the use of such terminology originated in connection with 2,4,6-triiodobenzoic acid derivatives possessing relatively high water solubility and/or relatively low toxicity, the results set forth herein are consistent with the view that substantially the same non-ionizing functions are also compatible with water solubility and/or low toxicity in the triiodinated moiety of the non-ionic compounds of the present invention.

Among the non-ionizing functions which may constitute X and Y may be mentioned the following: lower alkoxy, e.g., methoxy and ethoxy; hydroxy-(lower alkoxy), e.g., 2-hydroxy-ethoxy and 2,3-dihydroxy-propoxy; lower alkoxy-(lower alkoxy), e.g., methoxy-ethoxy and ethoxy-propoxy; lower acylamino, e.g., acetamido and propionamido; lower acylamino-(lower alkyl), e.g., acetaidomethyl and acetamido-ethyl; lower acylamino-(lower acylamino), e.g., aceturamido; hydroxy-lower acylamino, e.g., hydroxy-acetamido and gluconamido; N-(hydroxy lower alkyl)-lower acylamino, e.g., N-(2-hydroxyethyl)-acetamido and N-(2,3-dihydroxypropyl)-acetamido; N-(lower alkyl)lower acylamino, e.g., N-methylacetamido and N-methylpropionamido; lower alkylsulfonamido, e.g., methylsulfonamido and ethylsulfonamido; N-(lower alkyl)-lower alkylsulfonamido, e.g., N-methyl-ethylsulfonamido and N-ethyl-methylsulfonamido; 3,3-bis(lower alkyl)-ureido, e.g., 3,3-dimethylureido and 3-methyl-3-ethylureido; lower perfluoroacylamino, e.g., perfluoroacetamido and perfluoropropionamido; carbamyl; N-(lower alkyl)carbamyl, e.g., N-methylcarbamyl and N-ethylcarbamyl; N,N-di-(lower alkyl) carbamyl, e.g., N,N-dimethylcarbamyl and N,N-diethylcarbamyl; N-(hydroxy lower alkyl)carbamyl, e.g., N-(2-hydroxyethyl)carbamyl and N-(2,3-dihydroxypropyl)carbamyl; N-(hydroxy lower alkyl)-N-(lower alkyl)carbamyl, e.g., N-hydroxyethyl-N-methylcarbamyl and N-(2,3-dihydroxypropyl)-N-methylcarbamyl; lower alkoxy-(lower acylamino), e.g., methoxy-acetamido and ethoxyacetamido; lower alkoxy-alkoxy-(lower acylamino), e.g., methoxy-ethoxy-(acetamido) and ethoxy-methoxy(acetamido); hydroxy, hydroxy-lower alkyl, e.g., hydroxy-methyl, hydroxyethyl and 2,3-dihydroxypropyl. As used herein, the term "lower" (e.g., lower alkyl and lower alkoxy) means that the function contains between 1 and 6 carbon atoms. Those skilled in the art will recognize that functions of the above type other than those specifically enumerated may also constitute X and Y.

In a preferred embodiment of the invention, X is N-(hydroxy lower alkyl)-lower acylamino and more particularly the N-(2-hydroxyethyl)acetamido group while Y is one of the functions enumerated above.

In another aspect of the invention, one of X and Y may be constituted by hydrogen or one of the functions enumerated above and the other of X and Y may be constituted by the function

where R and CO—Z are as previously defined.

In the method aspect of the invention, the novel end products represented by the first structure previously set forth are prepared by first reacting an amine precursor compound of the formula:

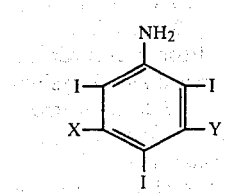

wherein X and Y are as defined above, with an acid halide of the formula

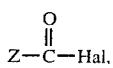

where Hal is chlorine or bromine and

is an ester, acetal or ketal derivative of an acyl residue of a polyhydroxy-monobasic acid of the type previously described. The hydroxyl groups of the parent polyhydroxy-monobasic acid have been protected prior to the preparation of the acid halide of such acid by converting them to ester, acetal or ketal groups. In this reaction, the acid halide reacts not only with the amino group of the precursor compound defined above but also with the hydroxy group or groups in the functions constituted by X, Y and R.

Exemplary of the ester protecting groups are formate, acetate, benzoate and cyclic carbonate, e.g.,

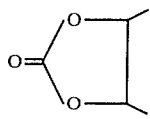

Other groups which may be used include thiocarbonate

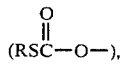

carbamate (NH$_2$CO—O—), phenylcarbamate (C$_6$H$_5$NHCO—O—) and phenylboronate

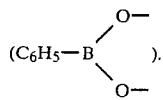

Thus, for example, typical acid halide compounds of the formula

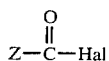

in which the protecting group is acetate include 2,3,4,5,6-penta-O-acetyl-D-gluconyl chloride, 2,3,4,5,6-penta-O-acetyl-L-mannonyl chloride, D-erythro-L-mannooctonyl chloride heptaacetate, D-erythro-L-gluco-octonyl chloride heptaacetate, D-manno-D-gala-heptonyl chloride hexaacetate, D-gala-L-manno-heptonyl chloride hexaacetate, D-gala-L-gluco-heptonyl chloride hexaacetate, D-gluco-D-gulo-heptonyl chloride hexaacetate, D-altronyl chloride pentaacetate, D-ribonyl chloride tetraacetate, D-galactonyl chloride pentaacetate, D-xylonyl chloride tetraacetate, L-arabonyl chloride tetraacetate and 2-acetamido-2-deoxy-D-gluconyl chloride tetraacetate.

Useful acetal and ketal protecting groups include benzylidene, methylene, cyclohexylidene, ethylidene, isopropylidene, tetrahydropyranoxy and similar groups (e.g.,

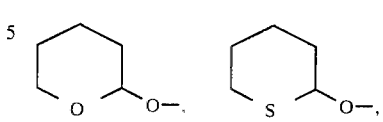

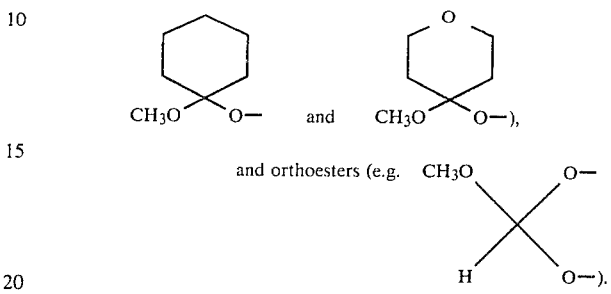

The acetal protecting groups include internal and external acetals and mixed internal and external acetals such as those exemplified by the acid halides 2,3:4,6-di-O-isopropylidene-2-keto-L-gulonyl chloride, 1,2:3,4-di-O-isopropylidenegalacturonyl chloride and the acid chloride of 2,3-O-isopropylidene-D-glyceric acid. While the D-compounds are generally more available commercially, it will be understood that the L-isomers or enantiomers may also be employed.

The reaction between the amine precursor compound and the acid halide produces intermediates of the formula:

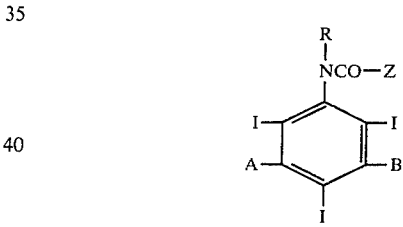

wherein CO—Z is an ester, acetal or ketal derivative of an acyl residue of a polyhydroxy-monobasic acid, said acyl residue containing not more than 8 carbon atoms in its chain or ring, each of A and B is a non-hydroxyl-containing, non-ionizing function compatible with water solubility and/or low toxicity in the 2,4,6-triiodophenyl configuration or is a derivative of an hydroxyl-containing, non-ionizing function compatible with water solubility and/or low toxicity in the 2,4,6-triiodophenyl configuration, in which derivative the hydroxyl groups have been converted to O—CO—Z groups and R is hydrogen or lower alkyl or is a derivative of an hydroxy (lower alkyl) group in which the hydroxyl groups have been converted to O—CO—Z groups. Such intermediates are converted into the end products of the invention by removal of the protecting groups from the intermediate compounds through treatment with acid where CO—Z is an acetal or ketal derivative or with base where CO—Z is an ester with simultaneous hydrolysis of any O—CO—Z groups in A or B.

In the preferred embodiment of the invention, the reaction between the amine precursor compound and the acid halide produces intermediates of the formula:

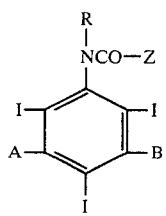

wherein B is a non-ionizing function compatible with water solubility and/or low toxicity in the 2,4,6-triiodophenyl configuration, CO—Z is selected from the group consisting of ester, acetal and ketal derivatives of an acyl residue of a polyhydroxy-monobasic acid, said acyl residue containing not more than 8 carbon atoms in its chain or ring, A is a derivative of an N-[hydroxy(lower alkyl)] lower acylamino group in which the hydroxyl groups have been converted to O—CO—Z groups and R is hydrogen or lower alkyl or is a derivative of an hydroxy (lower alkyl) group in which the hydroxyl groups have been converted to O—CO—Z groups. Such intermediates may be prepared in situ and converted into the desired end products of the invention as previously described without being isolated.

The novel compounds of the invention may be used as x-ray contrast agents in various radiographic procedures including those involving cardiovascular visualization, myelography, ventriculography, coronary arteriography, intravenous pyelography, bronchography and urography. Certain compounds of the invention exhibit high water solubility and relatively low toxicity while others exhibit the limited water solubility and relatively low toxicity required, for example, in oral radiographic procedures such as bronchography. The compounds of the invention may be produced in the form of exo/endo isomers which may influence their solubility characteristics. Certain of the compounds of the invention exhibit intracerebral and intracisternal toxicity values indicating suitability for use as x-ray contrast agents in the visualization of cerebrospinal cavities.

The following examples illustrate the invention.

EXAMPLE I

5-D-Gluconamido-2,4,6-triiodo-N,N'-dimethylisophthalamide

1. Preparation of 5-amino-2,4,6-triiodo-N-methylisophthalamyl chloride: II

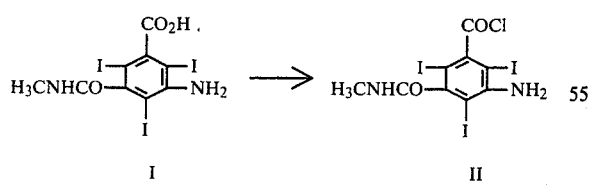

5-Amino-2,4,6-triiodo-N-methylisophthalamic acid (Hoey, U.S. Pat. No. 3,145,197, dated Aug. 18, 1964; I; 571 g., 1 mole) was refluxed in thionyl chloride (600 ml.) for one hour. Additional thionyl chloride (300 ml.) was added and reflux was continued for 3.5 hours. The homogeneous reaction mixture was concentrated under reduced pressure. The residue was dissolved in tetrahydrofuran (3 l.); the solution was washed with a cold saturated solution of sodium chloride and then with cold saturated sodium chloride-sodium carbonate solution until the aqueous layer remained basic. The organic layer was dried over sodium sulfate and evaporated to one-third its original volume. The precipitated solid was collected, washed with tetrahydrofuran and dried, 235 g. (53%). The product was homogeneous by thin-layer chromatography (chloroformethyl acetate-acetic acid, 30:20:1) and its structure was confirmed by infrared spectroscopy.

2. Preparation of 5-amino-2,4,6-triiodo-N,N'-dimethylisophthalamide, III

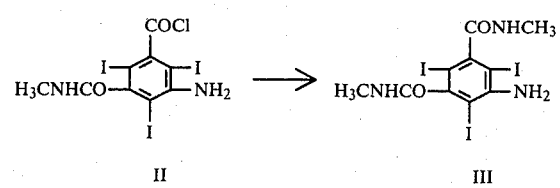

To a 0°–5° C. solution of 40% aqueous monomethylamine (560 g.; 7.2 moles) was slowly added a solution of 5-amino-2,4,6-triiodo-N-methylisophthalamyl chloride (II; 225 g., 0.38 mole) in tetrahydrofuran (1.5 l.). The resulting mixture was stirred for 2.5 hours after which the precipitated solid was collected, reslurried in dilute sodium carbonate solution and then methanol, and dried (190 g.) (85%). The product, m.p. 265°–271° C. (dec.), was homogeneous by thin-layer chromatography (ethyl acetate-acetic acid, 98:2) and its structure was confirmed by infrared spectroscopy and nuclear magnetic resonance spectroscopy.

3. Preparation of 2,3,4,5,6-O-Pentaacetylgluconyl-chloride 2,3,4,5,6-penta-O-acetyl gluconyl chloride (or 2,3,4,5,6-O-pentaacetylgluconyl chloride) was prepared by the method of C. E. Braun and C. D. Cook, *Organic Synthesis*, 41, 79 (1961).

4. Preparation of 5-(2,3,4,5,6-O-Pentaacetylgluconamido)-2,4,6-triiodo-N,N'-dimethylisophthalamide; IV

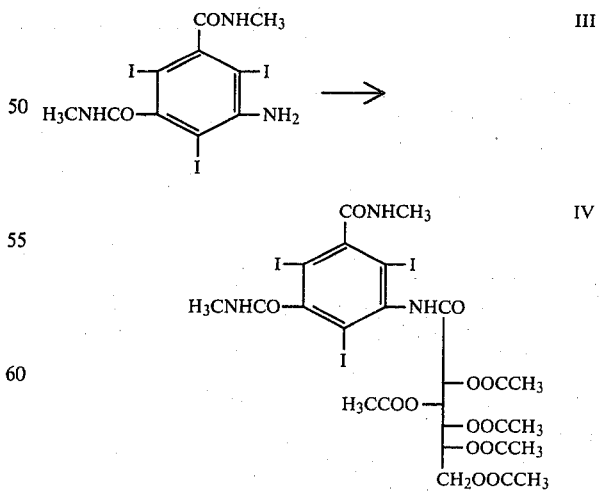

5-Amino-2,4,6-triiodo-N,N'-dimethylisophthalamide (III; 58.5 g., 0.1 mole) was dissolved with heating in dimethylacetamide (500 ml.). The solution was allowed to cool to 25° C. at which time 2,3,4,5,6-O-pentaacetylgluconyl chloride (127.3 g., 0.3 mole) was added in one portion. The reaction mixture was stirred at 25° C. for 114 hours; the solvent was removed under reduced pressure. The oily residue was triturated in water (2 l.) for 5.5 hours; the resulting solid was collected, washed with water and dried at 70° C. (73.84 g., 76% crude). The crude product was recrystallized from methanol-ether which yielded two crops totaling 49.7 g. (51%).

The analytical data were obtained on a small sample purified separately; m.p. 273°–274° C. (dec.). The product was homogeneous by thin-layer chromatography (ethyl acetate-acetic acid, 98.2) and its structure was confirmed by infrared spectroscopy and nuclear magnetic resonance spectroscopy.

Calc. for $C_{26}H_{30}I_3N_3O_{13}$: C, 32.09; H, 3.11; I, 39.12; N, 4.32. Found: C, 32.27; H, 3.36; I, 38.88; N, 4.31.

5. Preparation of 5-D-Gluconamido-2,4,6-triiodo-N,N'-dimethylisophthalamide; V

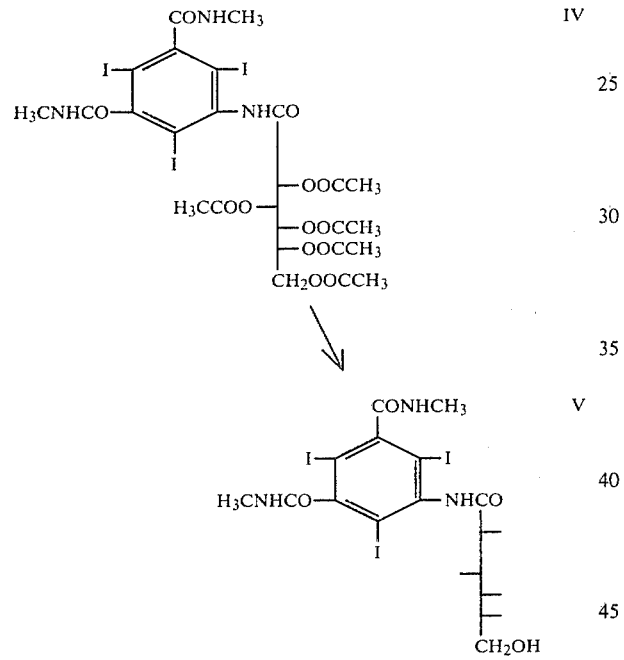

5-(2,3,4,5,6-O-Pentaacetylgluconamido)-2,4,6-triiodo-N,N'-dimethylisophthalamide (IV, 42.57 g.; 0.044 mole) was suspended in 2.2 l. of a 1:1 mixture of methanol-water. Sodium carbonate (11.7 g.; 0.11 mole) was then added in one portion. After one hour stirring at room temperature, the reaction mixture was passed through a column containing 500 ml. of an ion-exchange resin marketed under the trade designation "IR-120" ($H^\oplus$, 1.9 meq. $H^\oplus$/ml). The solvent was then evaporated under reduced pressure. The resulting colorless solid was triturated in boiling methanol for 45 minutes. After standing overnight, the solid was collected and dried at 70° C. under vaccuum, 22.3 g. A second crop was obtained from the mother liquor, 6.7 g. The total product, 29 g., represents an 86.5% yield. Recrystallization ( a small sample prepared earlier was used) from methanol gave analytically pure material, m.p. 248.5°–249° C. (dec.; corr.). The product was homogeneous by thin-layer chromatography (ethyl acetate-methanolacetic acid, 78:20:2) and its structure was confirmed by infrared spectroscopy and nuclear magnetic resonance spectroscopy. The water solubility of the compound was determined to be 1.2% (w/v).

Calc. for $C_{16}H_{20}I_3N_3O_8$: C, 25.18; H, 2.64; I, 49.89; N, 5.51. Found: C, 25.24; H, 2.81; I, 49.64; N, 5.37.

EXAMPLE II

5-D-Gluconamido-2,4,6-triiodo-N,N',N'-trimethylisophthalamide

1. Preparation of 5-amino-2,4,6-triiodo-N-methylisophthalamyl chloride; II

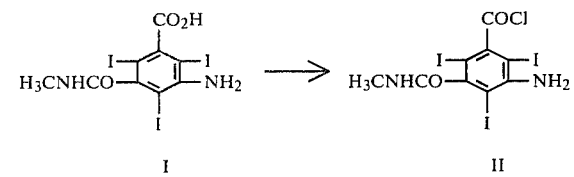

5-Amino-2,4,6-triiodo-N-methylisophthalamic acid (Hoey, U.S. Pat. No. 3,145,197, dated Aug. 18, 1964; I; 572 g., 1.0 mole) was heated and stirred at reflux temperature in thionyl chloride (1.2 l.) for 4.5 hours. After concentration of the homogeneous reaction mixture under reduced pressure, the residue was dissolved in tetrahydrofuran (2.0 l.) and the cooled solution was extracted with a saturated solution of sodium carbonate and sodium chloride. The layers were separated and the organic layer was dried over sodium sulfate. The organic layer was used directly to provide 5-amino-2,4,6-triiodo-N,N',N'-trimethylisophthalamide; III 2. Preparation of 5-Amino-2,4,6-triiodo-N,N',N'-trimethylisophthalamide; III

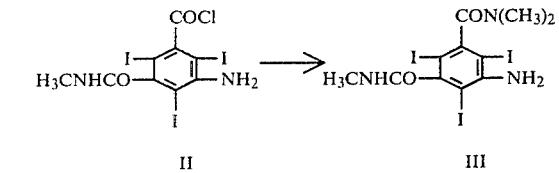

To chilled 25% aqueous dimethylamine (1.3 l.) was added the solution of the acid chloride (II) (1.0 mole) prepared as above in tetrahydrofuran while maintaining the solution at 20° C. After stirring overnight in an open beaker, the precipitated product (287 g., representing a yield of 48%) was collected by filtration and washed with methanol. A second crop of 111 g. (18.5%) was obtained from the mother liquor. The product, m.p. 259°–263° C. (dec.), was homogeneous by thin-layer chromatography (ethyl acetate-acetic acid 98:2) and its structure was confirmed by infrared spectroscopy and nuclear magnetic resonance spectroscopy.

Calc. for $C_{11}H_{12}I_3N_3O_2$: C, 22.06; H, 2.06; I, 63.56; N, 7.02. Found: C, 22.06; H, 2.17; I, 64.24; N, 6.90; C, 21.80; H, 2.06; I, 63.95; N, 6.94.

3. Preparation of 2,3,4,5,6-O-Pentaacetylgluconyl Chloride 2,3,4,5,6-O-pentaacetylgluconyl chloride was prepared by the method of C. E. Braun and C. D. Cook, *Organic Synthesis*, 41, 79 (1961).

4. Preparation of 5-(2,3,4,5,6-O-Pentaacetylgluconamido)-2,4,6-triiodo-N,N,N′-trimethylisophthalamide; IV

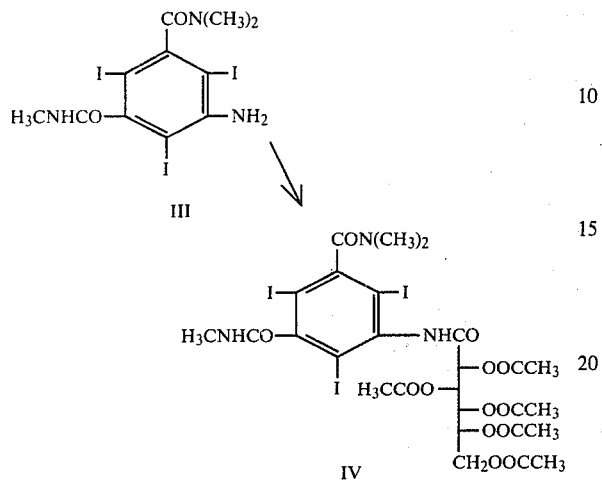

To 5-Amino-2,4,6-triiodo-N,N,N′-trimethylisophthalamide (III; 90 g., 0.15 mole) dissolved in dimethylacetamide (750 ml.) was added in one portion 2,3,4,5,6-O-pentaacetylgluconyl chloride (191 g., 0.45 mole). After 66 hours at room temperature, the reaction mixture was concentrated under reduced pressure. To the residue was added water (1 l. ); the resulting solution was extracted with chloroform (500 ml.; 2×250 ml.). To the combined extracts was added additional chloroform (500 ml.). The chloroform solution was washed with 5% aqueous sodium bicarbonate solution (2×500 ml.), 1 N hydrochloric acid (600 ml.), water (600 ml.) and saturated brine solution (600 ml.); then it was dried over magnesium sulfate and evaporated under reduced pressure. The resulting oil was crystallized from toluene, 71 g. (40%). Assay by thin-layer chromatography (ethyl acetate-acetic acid, 98.2) showed two spots (IV plus partially hydrolyzed, i.e., deprotected, material). The crude product was saponified without further purification.

5. Preparation of 5-D-Gluconamido-2,4,6-triiodo-N,N,N′-trimethylisophthalamide: V

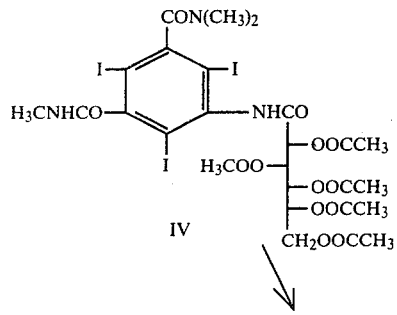

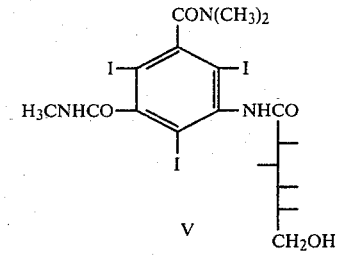

To 5-(2,3,4,5,6-O-Pentaacetylgluconamido)-2,4,6-triiodo-N,N,N′-trimethylisophthalamide; (IV; 69.5 g.; 0.071 mole) dissolved in 3.5 l. of a 1:1 methanol-water mixture was added sodium carbonate (18.5 g.; 0.176 mole). After one hour at room temperature, the reaction mixture was passed through a column containing 1000 ml. of an ion-exchange resin marketed under the trade designation "IR-120" (H⊕; 1.75 meq./ml.). The solvent was then removed under reduced pressure. The resulting material was recrystallized from methanol-ether yielding two crops (25.7 g., m.p. 213°–216° C. and 16.9 g., m.p. 199°–203° C.). It was found that the second crop contained methanol of crystallization. Therefore, 12.8 g of the second crop was dissolved in water (1.1 l.), and the solution was evaporated under reduced pressure yielding 12.6 g. of an amorphous product (m.p. 174°–185° C.). Spectroscopic, thin-layer chromatography and gas-liquid chromatography analysis showed the crops to be equivalent and free of methanol. The combined crops (38.3 g.) represent a 70% yield. An analytical sample was prepared by recrystallization (material from an earlier small run was used) for methanol-ether; m.p. 217°–225° C. The product was homogeneous by thin-layer chromatography (ethyl acetate-methanol-acetic acid, 78:20:2 and chloroform-isopropyl alcohol-acetic acid, 50:50:1) and its structure was confirmed by infrared spectroscopy and nuclear magnetic resonance spectroscopy. The water solubility of the compound was determined to be 28.4% (w/v).

Calc. for $C_{17}H_{23}I_3N_3O_8$:C, 26.27; H, 2.85; I, 48.99, N, 5.41. Found: C, 26.32; H, 3.10; I, 48.65; N, 5.51.

EXAMPLE III 2,4,6-Triiodo-5-(2-keto-L-gulonamido)-N,N,N′-trimethylisophthalamide

1. Preparation of 2,3,4,6-Di-O-isopropylidene-2-keto-L-gulonyl chloride: II

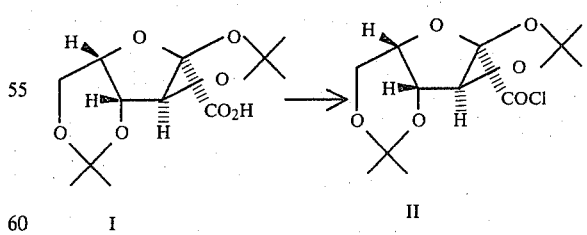

The procedure employed was a modification of that of C. L. Mehltretter, J. Am. Chem. Soc., 69, 2133 (1947). 2,3:4,6-Di-O-isopropylidene-2-keto-L-gulonic acid monohydrate (I) was dried by azeotropic distillation with chloroform. To the anhydrous acid (82.2 g.; 0.3 mole) dissolved in anhydrous ether (500 ml.) was added slowly in small portions phosphorous pentachloride (62.4 g.; 0.3 mole). The reaction mixture was stirred at room temperature for 19 hours; the solvent was then removed under reduced pressure yielding a dark brown syrup, 85 g. (96.5%). The structure of the product was confirmed by infrared spectroscopy and nuclear magnetic resonance spectroscopy.

2. Preparation of 5-Amino-2,4,6-triiodo-N,N,N'-trimethylisophthalamide; III

See Example II 2.

3. Preparation of 2,4,6-Triiodo-5-(2,3:4,6-di-O-isopropylidene-2-keto-L-gulonamido)-N,N,N'-trimethylisophthalamide; IV

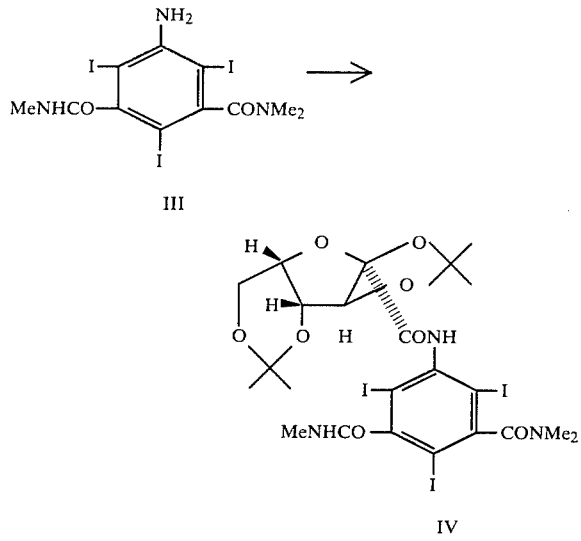

To 5-amino-2,4,6-triiodo-N,N,N'-trimethylisophthalamide (III; 58 g.; 0.097 mole) dissolved in dimethylacetamide (460 ml.) was added 2,3:4,6-di-O-isopropylidene-2-keto-L-gulonyl chloride (II; 85 g.; 0.29 mole) in dimethylacetamide (230 ml.). After 160.5 hours at room temperature, the reaction mixture was poured into a 10% aqueous sodium bicarbonate solution (500 ml.). The resulting solution was stirred for 3 hours and then extracted with chloroform (3×500 ml.). The combined extracts were dried over sodium sulfate and evaporated under reduced pressure. The foam-like product was triturated in ether (1 l.) overnight. The resulting solid was collected and dried at 70° C. in vacuo, 74.5 g. (90%). The product was homogeneous by thin-layer chromatography (ethyl acetate-acetic acid, 98:2) and the identity of the product was confirmed by infrared and nuclear magnetic resonance spectroscopy.

4. Preparation of 2,4,6-Triiodo-5-(2-keto-L-gulonamido)-N,N,N'-trimethylisophthalamide; V

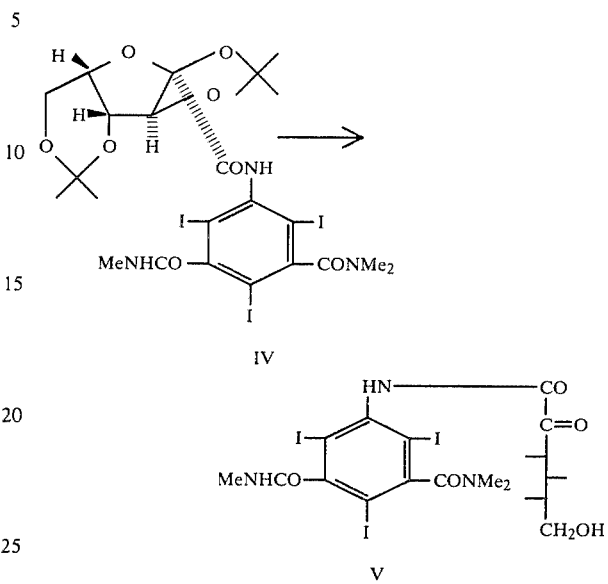

2,4,6-Triiodo-5-(2,3:4,6-di-O-isopropylidene-2-keto-L-gulonamido)-N,N,N'-trimethylisophthalamide (IV; 27 g.; 0.032 mole) was refluxed for 16 hours in a mixture of water (450 ml.), dioxane (270 ml.) and trifluoroacetic acid (4.5 ml). The solvent was removed under reduced pressure. The residue was triturated in refluxing methanol for 0.5 hr. and the suspension was allowed to cool overnight. The suspended solid was collected, washed with methanol (50 ml.) and dried at 60° C. in vacuo, 15.5 g. (63%), m.p. 248°–250° C. (dec.; corr.). The product was homogeneous by thin-layer chromatography (chloroform-isopropyl alcohol, 60:40). The infrared and nuclear magnetic resonance spectra were consistent with the structure assigned. The water solubility of the compound was determined to be 3.75% (w/v).

Calc. for $C_{17}H_{20}I_3N_3O_8$: C, 26.36; H, 2.60; I, 49.12; N, 5.42. Found: C, 26.30; H, 2.58; I, 49.10; N, 5.26; C, 26.03; H, 2.63; I, 49.33; N, 5.21.

EXAMPLE IV

3-D-Gluconamido-2,4,6-triiodo-N-methyl-5-(N-methylacetamido) benzamide

1. Preparation of 3-Amino-2,4,6-triiodo-5-(N-methylacetamido)-benzoic acid; II

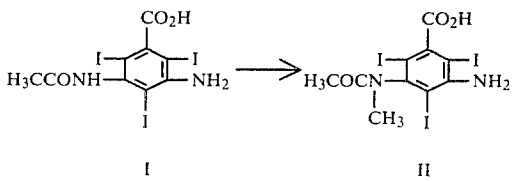

3-Acetamido-5-amino-2,4,6-triiodobenzoic acid (I; 228.76 g., 0.4 mole) was added to an anhydrous ethanolic solution of sodium ethoxide (prepared from 18.4 g. (0.8 g. atom) of sodium) at 45° C. After 10 minutes, the homogeneous solution was cooled to 22° C. and methyl iodide (62.48 g.; 0.44 mole) was added. The reaction mixture was heated at 50°-55° C. for 30 minutes, at 62° C. for 30 minutes and finally at 68°-70° C. for 15 minutes. The reaction mixture was now pH 8. Methyl iodide (1 ml.) was added and heating was continued at 70° C. for 15 minutes after which the solution was neutral. The ethanol was removed under reduced pressure and water (1300 ml.) was added to the residue. The solid which dropped out of solution was collected; the filtrate was basified (~pH 10) with 50% sodium hydroxide and was washed with a 3:1 chloroform-isopropyl alcohol mixture (800 ml.). The aqueous layer was acidified to pH 5 with acetic acid and treated with activated charcoal marketed under the trade designation "Darco G-60" (5 g.) for 1 hour. The filtered solution was added to 6 N hydrochloric acid (700 ml.) at room temperature to precipitate the product. The precipitate was digested for 10 minutes and was then collected, washed with water (500 ml.), and dried at 60° C. overnight to yield 193.5 g. of 3-amino-2,4,6-triiodo-5-(N-methylacetamido)benzoic acid (82.6% yield). The product was homogeneous by thin-layer chromatography (chloroform-ethyl acetateacetic acid, 30:20:1) and the structure of the product was confirmed by nuclear magnetic resonance spectroscopy.

2. Preparation of 3-Amino-2,4,6-triiodo-5-(N-methylacetamido)-benzoyl chloride: III

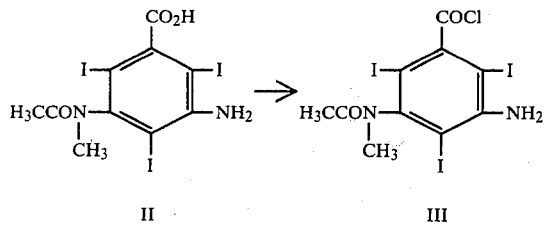

The procedure employed was essentially that set forth in U.S. Pat. No. 3,701,771, dated Oct. 31, 1972.

3. Preparation of 3-Amino-2,4,6-triiodo-N-methyl-5-(N-methylcarbamyl)-acetanilide; IV

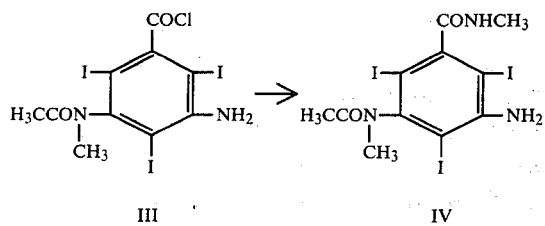

3-Amino-2,4,6-triiodo-5-(N-methylacetamido)benzoyl chloride (III; 52.4 g.; 0.087 mole) was dissolved in tetrahydrofuran (225 ml.). The tetrahydrofuran solution was then added slowly to 40% aqueous methylamine (201.5 g.) (i.e., 80.6 g. or 2.6 moles of methylamine) at 0°-5° C. After the addition was complete, the reaction mixture was stirred at 0°-5° C. for an additional 15 minutes and then overnight at room temperature open to the air. The precipitated solid was collected, washed with water and dried at 60° C. under vacuum to give 41.75 g. (80% yield) of product. Recrystallization from methanol gave analytically pure material, m.p. 244.5°-247° C. (dec.; corr.). The product was homogeneous by thin-layer chromatography (ethyl acetate-chloroform-acetic acid, 30:20:1) and the structure of the product was confirmed by infrared and nuclear magnetic resonance spectroscopy.

Calc. for $C_{11}H_{12}I_3N_3O_2$: C, 22.06; H, 2.02; I, 63.57; N, 7.02. Found: C, 21.95; H, 2.18; I, 63.52; N, 7.17; C, 21.92; H, 2.07; I, 63.72; N, 7.20.

4. Preparation of 2,3,4,5,6-O-Pentaacetylgluconyl Chloride 2,3,4,5,6-O-pentaacetylgluconyl chloride was prepared by the method of C. E. Braun and C. D. Cook, *Organic Synthesis*, 41, 79 (1961).

5. Preparation of 3-(2,3,4,5,6-O-Pentaacetylgluconamido)-2,4,6-triiodo-N-methyl-5-(N-methylacetamido)benzamide; V

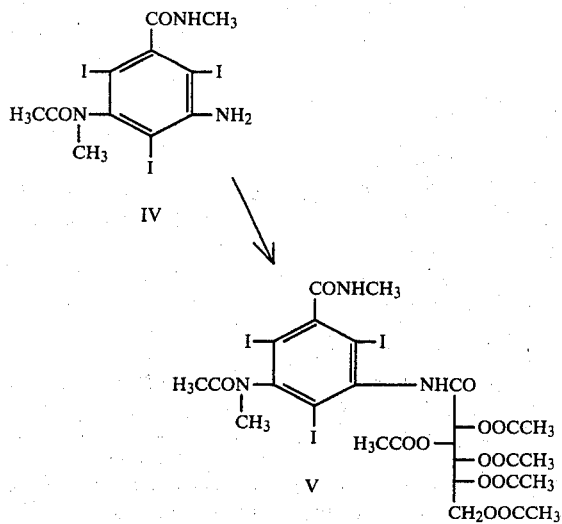

To 3-amino-2,4,6-triiodo-N-methyl-5-(N-methylcarbamyl)-acetanilide (IV; 90 g., 0.15 mole) dissolved in dimethylacetamide (900 ml.) was added in one portion 2,3,4,5,6-O-pentaacetylgluconyl chloride (127.35 g.; 0.3 mole). After 67.5 hrs. at room temperature, the reaction mixture was poured into water (1500 ml.) and the resulting solution was stirred for 1.25 hr. The aqueous solution was extracted with chloroform (3×1000 ml.); the combined extracts were washed with 5% aqueous sodium bicarbonate (2×1000 ml.), dried over sodium sulfate, and evaporated under reduced pressure. The oily solid obtained was triturated in ether (1150 ml.) for four days; the resulting solid was collected, washed with ether, and dried under vacuum at 60° C. to give 126.96 g. (86%). Thin-layer chromatography (ethyl acetate-chloroform-acetic acid, 40:10:1) showed a major and a minor spot (compound V plus partially hydrolyzed, i.e., deprotected, material). The crude product was saponified without further purification.

6. Preparation of 3-D-Gluconamido-2,4,6-triiodo-N-methyl-5-(N-methylacetamido)-benzamide, VI

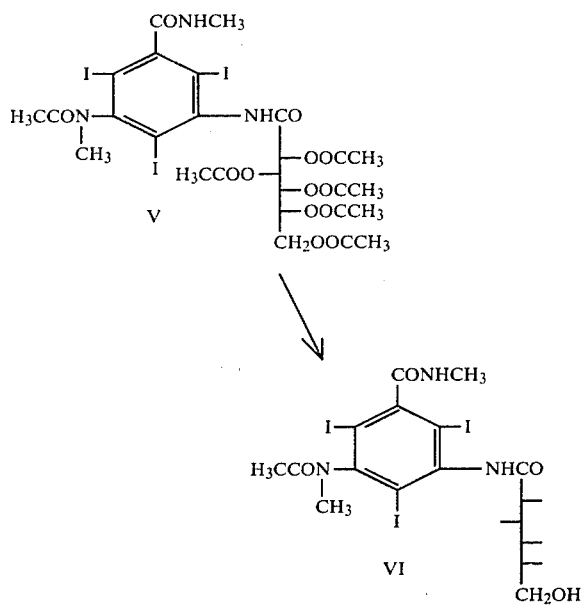

3-(2,3,4,5,6l-O-Pentaacetylgluconamido)-2,4,6-triiodo-N-methyl-5-(N-methylacetamido)-benzamide (V; 98.7 g.; 0.1 mole) was dissolved in a 1:1 mixture of methanol-water (5 l.). Sodium carbonate (26.5 g., 0.25 mole) was then added in one portion. After 2 hours the reaction mixture was passed through a column containing 1170 ml. of an ion-exchange resin marketed under the trade designation "IR-120" (1.75 meq. H⊕/ml.). The solvent was then removed under reduced pressure yielding 71 g. of a foam-like solid. This material was taken up in water (500 ml.); the solution was filtered to remove trace insolubles. The aqueous solution was extracted with chloroform-isopropyl alcohol (3:1; 7×200 ml.) with the contact time of each extraction being 30–60 minutes. The aqueous solution was treated with activated carbon marketed under the trade designation "Darco G-60" (2.5 g.) for two hours, filtered, and stripped to dryness resulting in 43 g. (53% yield) of a foam-like solid. A portion of the crude product (30.3 g.) was dissolved in water (450 ml.). Sodium hydroxide (0.1 N; 38 ml.) was added until the pH of the solution remained slightly basic (pH~7.3) for at least 10–15 minutes. The solution was then stirred overnight during which time the pH dropped to 5.25; an additional 2.5 ml. of 0.1 N sodium hydroxide was added to pH 7. The solution was extracted with 90% aqueous phenol (4×100 ml.). The combined phenolic extracts were washed with water (4×100 ml.); an emulsion formed each time, but it was broken by the addition of 15 drops of 3 N hydrochloric acid. The phenolic solution was diluted with ether (1200 ml.) and then extracted with water (4×100 ml.). The combined aqueous extracts were washed with ether (4×100 ml.), treated with 0.9 g. (3%) of activated carbon ("Darco G-60") for two hours at room temperature, filtered and evaporated under reduced pressure at 60° C. yielding 27.2 g. of 3-gluconamido-2,4,6-triiodo-N-methyl-5-(N-methylacetamido)-benzamide, VI, m.p. 166°–177° C. Thin-layer chromatography (ethyl acetate-methanol-acetic acid, 80:20:2) produced two spots probably indicating isomers. The water solubility of the product was determined to be ≧100% (w/v). Elemental analysis was carried out on a small sample previously taken through the phenol extraction; the sample melted at 165°–177° C.

Calc. for $C_{17}H_{22}I_3N_3O_8$: C, 26.27; H, 2.85; I, 48.99; N, 5.41. Found: C, 26.03; H, 2.85; I, 49.02; ;1 N, 5.50; C, 26.08; H, 2.88; I, 49.11; N, 5.42.

EXAMPLE V 2,4,6-Triiodo-N,N,N'-trimethyl-5-(N-methyl-D-galacturonamido)-isophthalamide

1. Preparation of 5-(1,2:3,4-di-O-isopropylidenegalacturonamido)-2,4,6-triiodo-N,N,N'-trimethylisophthalamide; II

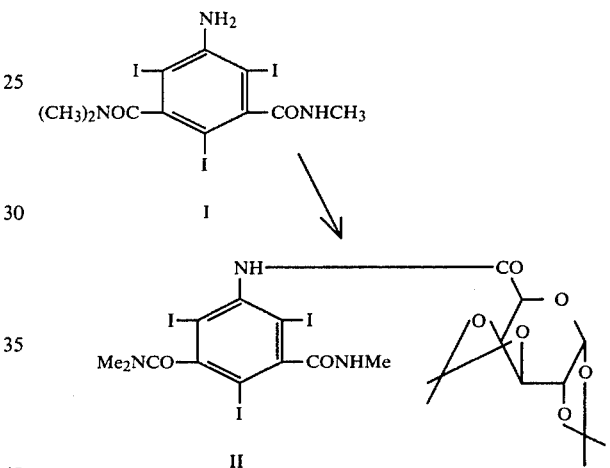

To 5-amino-2,4,6-triiodo-N,N,N'-trimethylisophthalamide (I; 11.98 g., 0.02 mole) dissolved in dimethylacetamide (120 ml.) was added in one portion 1,2:3,4-di-O-isopropylidenegalacturonyl chloride (prepared by the method of G. S. Bylina and L. R. Uvarova, *Zhurnal Organicheskoi Khimmi*, 8, 2520 (1972) (8.78 g.; 0.03 mole). After 116 hours at 50° C., the reaction mixture was cautiously poured into 5% aqueous sodium bicarbonate (100 ml.); the solution was stirred for 0.5 hr. after which time a solid had dropped out. Water (50 ml.) was added to dissolve the solid and the resulting solution was extracted with chloroform (3×50 ml.). The combined extracts were washed with 5% aqueous sodium bicarbonate (100 ml.), water (100 ml.), dried over sodium sulfate and evaporated to near dryness under reduced pressure. Ether (200 ml.) was added and the mixture was vigorously stirred overnight; the resulting solid was collected, and dried under vacuum at 60° C., 12.48 g. (73%). This product contained some dimethylacetamide as was shown by nuclear magnetic resonance spectroscopy.

2. Preparation of 5-(1,2:3,4-di-O-isopropylidene-N-methylgalacturonamido)-2,4,6-triiodo-N,N′-trimethylisophthalamide; III

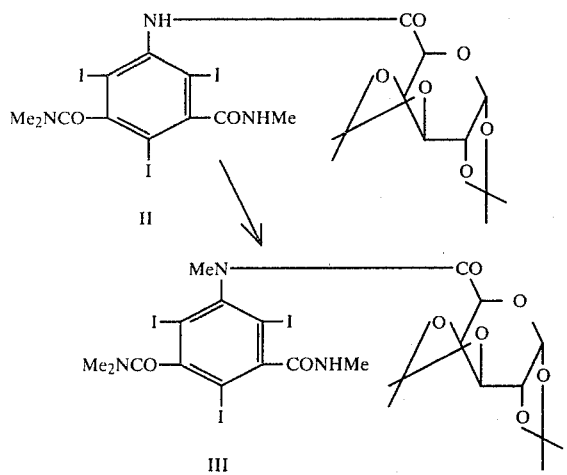

Sodium metal (1.8 g.; 0.078 mole) was dissolved in anhydrous ethanol (215 ml.) under a nitrogen atmosphere. The solution was heated to 45° C. and 5-(1,2:3,4-di-O-isopropylidenegalacturonamido)-2,4,6-triiodo-N,N,N′-trimethylisophthalamide (II; 67 g.; 0.078 mole) was added in one portion. The resulting, deep red solution was heated at 45°–50° C. for 35 min. and was then cooled in an ice bath to 5° C. The pH of the solution was approximately 10. Methyl iodide (114 g.; 0.8 mole) was added and the reaction mixture was heated at 50°–55° C. for 35 min. The pH of the solution was now 6–7 indicating complete reaction.

The reaction mixture was concentrated under reduced pressure. The residue was slurried in chloroform (500 ml.) for 15 min. The suspension was then filtered; the filter cake was washed with chloroform (100 ml.). The combined filtrate and washings were washed with water (2×200 ml.), dried over sodium sulfate and evaporated in vacuo yielding 69.26 g. (>100%—the product contained residual solvent according to nuclear magnetic resonance spectroscopy) of III as a yellow foam like solid; thin-layer chromatography (ethyl acetate-chloroform-acetic acid, 40:10:1) showed three spots presumably due to isomers; the nuclear magnetic resonance spectra was consistent with the assigned structure. The product was hydrolyzed without further purification.

3. Preparation of 2,4,6-triiodo-N,N,N′-trimethyl-5-(N-methyl-D-galacturonamido)-isophthalamide; IV

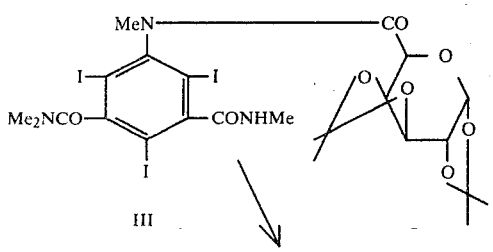

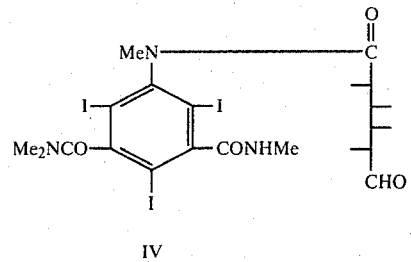

5-(1,2:3,4-di-O-isopropylidene-N-methylgalacturonamido)-2,4,6-triiodo-N,N,N′-trimethylisophthalamide (III; 68.46 g.; 0.079 mole) was suspended in a mixture of dioxane (684.6 ml.) and water (1141 ml.). Trifluoroacetic acid (11.4 ml.) was added and the mixture was refluxed for 3 hr. The reaction mixture was concentrated in vacuo. The residue was dissolved in water (1 l.); the pH of the solution was adjusted to 7 with dilute sodium hydroxide. The solution was extracted with 90% aqueous phenol (4×100 ml.; contact time 10 min.); the combined phenolic extracts were washed with water (4×100 ml.). The phenolic layer was diluted with ether (1200 ml.); the etheral solution was extracted with water (4×100 ml.). The combined aqueous extracts were washed with chloroform-isopropyl alcohol mixtures (95:5, 7×100 ml.; contact time 30 min. and 90:10, 4×100 ml.; contact time 30 min.), treated with activated carbon ("Darco G-60", 1.8 g.) overnight, and evaporated under reduced pressure employing a hot water bath yielding 45.77 g. (73.5%) of IV as an off-white, foam-like solid, m.p. 207° C. (sl. dec.), 231°–245° C. (dec.); the infrared spectrum and thin-layer chromatography results were identical to those given below for the analytical sample.

Analytical data were obtained on a small sample prepared in the manner described above. The melting point was 187° C. (sl. dec.), 231°–243° (dec.). The infrared and nuclear magnetic resonance spectra were consistent with the assigned structure. Thin-layer chromatography (chloroform-methanol-acetic acid, 80:20:2) showed four spots indicating isomers; the water solubility was determined to be ≧100% (w/v).

Calc. for $C_{18}H_{22}I_3N_3O_8$: C, 27.40; H, 2.81; I, 48.25; N, 5.33. Found: C, 27.54; H, 3.00; I, 48.06; N, 5.22.

EXAMPLE VI

3-Acetamido-5-D-gluconamido-2,4,6-triiodo-N-methylbenzamide

1. Preparation of 3-acetamido-5-amino-2,4,6-triiodo-N-methylbenzamide; III

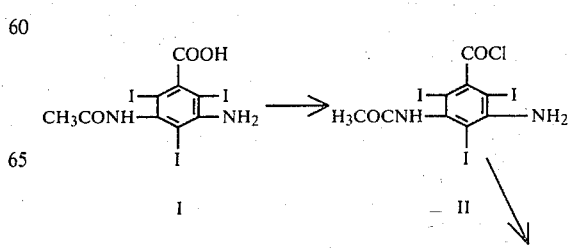

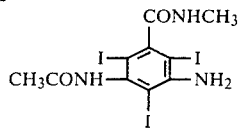

3-Acetamido-5-amino-2,4,6-triiodobenzoic acid (I; 57.2 g.; 0.1 mole) was suspended in dimethylacetamide (171 ml.). Thionyl chloride (26.1 g.; 0.22 mole) was then added slowly at 0°–10° C. After being stirred for two days at room temperature, 136.65 g. of 40% aqueous methylamine (i.e., 54.66 g. or 1.76 moles of methylamine) was added slowly at 0°–10° C. After stirring overnight at room temperature, the mixture was concentrated in vacuo. The residue was dissolved in water (500 ml.) and the mixture was stirred for three days. The precipitated solid was collected, dried and then reslurried for 1 hr. in methanol (140 ml.) at reflux. After cooling overnight, the suspended solid was collected and dried, 10.66 g. (18%).

Recrystallization from methanol gave analytically pure material, m.p. 210°–222° C. (dec.). The product was homogeneous by thin-layer chromatography (ethyl acetate-chloroform-acetic acid, 40:10:1). Infrared and nuclear magnetic resonance spectra were consistent with the assigned structure.

Calc. for $C_{10}H_{10}I_3N_3O_2$: C, 20.53; H, 1.72; I, 65.09; N, 7.18. Found: C, 20.58; H, 1.93; I, 65.25; N, 6.38.

2. Preparation of 3-acetamido-2,4,6-triiodo-N-methyl-5-(2,3,4,5,6-O-pentaacetylgluconamido)-benzamide; IV

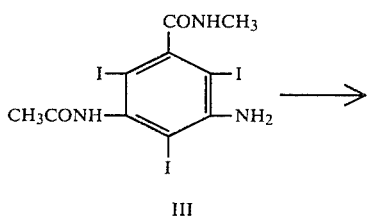

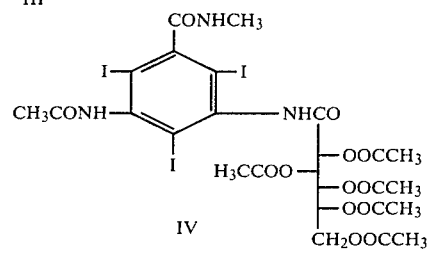

To 3-acetamido-5-amino-2,4,6-triiodo-N-methylbenzamide (III; 87.75 g.; 0.15 mole) dissolved in dimethylacetamide (900 ml.) was added in one portion 2,3,4,5,6-O-pentaacetylgluconyl chloride (Example I 3; 127.3 g.; 0.3 mole). After six days at room temperature, the reaction mixture was poured into water (500 ml.). After stirring for two hours, the aqueous mixture was extracted with chloroform (4×250 ml.). The combined organic extracts were washed with 5% aqueous sodium bicarbonate (3×500 ml.), dried over sodium sulfate, and evaporated under reduced pressure. The residue was taken up in chloroform (500 ml.), and the solution was stored at room temperature overnight. The precipitated solid was collected and dried, 106.08 g. (72.5%); the product was homogeneous by thin-layer chromatography (ethyl acetate-chloroform-acetic acid, 40:10:1); the infrared and nuclear magnetic resonance spectra were consistent with the assigned structure. The material was hydrolyzed without further purification.

3. Preparation of 3-acetamido-5-D-gluconamido-2,4,6-triiodo-N-methylbenzamide; V

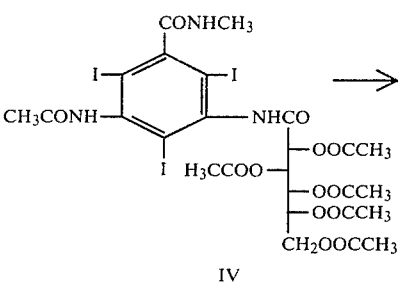

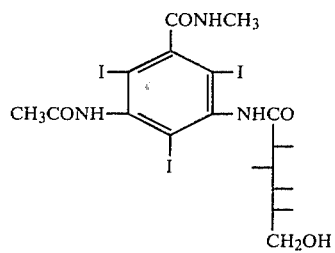

To a stirred mixture of 3-acetamido-2,4,6-triiodo-N-methyl-5-(2,3,4,5,6-O-pentaacetylgluconamido)-benzamide (IV; 9.73 g., 0.01 mole) in 50 ml. of a 1:1 mixture of methanol and water was added in one portion sodium carbonate (2.65 g.; 0.025 mole). After 1 hour, 3 g. (0.05 mole) of glacial acetic acid diluted with water (9 ml.) was added, and the mixture was passed through a column containing 143 ml. of an ion-exchange resin marketed under the trade designation "1R-120" (1.75 meq. H+/ml.). The solvent was removed under reduced pressure. The residue was taken up in water (70 ml.); the aqueous solution was extracted with chloroform-isopropyl alcohol mixtures (3:1; 3×20 ml., then 5×100 ml.; contact time 30 min.), and was then evaporated to dryness. The residue was recrystallized from methanol (140 ml.). The solid was dissolved in water (250 ml.), and the solution was evaporated under reduced pressure resulting in 5.21 g. (68.5%) of V as a colorless, foam-like solid; m.p. 212°–222° C. (dec.). The product was homogeneous by thin-layer chromatography (chloroform-methanol-acetic acid; 80:20:2). Its water solubility was determined to be 8.6% (w/v). The infrared and nuclear magnetic resonance spectra were consistent with the assigned structure.

Calc. for $C_{16}H_{20}I_3N_3O_8$: C, 25.18; H, 2.64; I, 49.90; N, 5.51. Found: C, 25.22; H, 2.72; I, 49.84; N, 5.63.

EXAMPLE VII

3-D-Gluconamido-5-hydroxymethyl-2,4,6-triiodo-N-methylbenzamide

1. Preparation of 3-amino-5-hydroxymethyl-2,4,6-triiodo-N-methylbenzamide; II

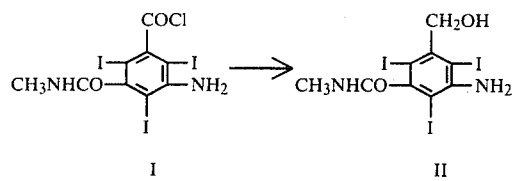

5-Amino-2,4,6-triiodo-N-methylisophthalamyl chloride (Example II; II: 5.9 g.; 0.01 mole) dissolved in diglyme (75 ml.) was added slowly to a suspension of sodium borohydride (0.757 g.; 0.02 mole) in diglyme (25 ml.) under nitrogen at room temperature. After stirring overnight, the reaction mixture was poured into water (200 ml.) which was then acidified (pH3) with dilute hydrochloric acid. The aqueous solution was extracted with chloroform (3×100 ml.); the combined organic extracts were washed with 5% aqueous sodium bicarbonate, quickly dried over sodium sulfate, filtered, and stored at room temperature for 30 min. The precipitated solid (probably deiodinated material) was collected; the filtrate was concentrated to one-fourth its volume and stored at room temperature overnight. The precipitated solid was collected and dried at 60° C., 1.55 g. (28%). Recrystallization from methanol gave analytically pure material; m.p. 208°–210° C. (dec.). The product was homogeneous by thin-layer chromatography (chloroform-ethyl acetate-acetic acid, 30:20:1). The infrared and nuclear magnetic resonance spectra were consistent with the assigned structure.

Calc. for $C_9H_9I_3N_2O_2$:C, 19.37; H, 1.63; I, 68.24; N, 5.02. Found: C, 19.36; H, 1.77; I, 68.28; N, 5.00.

2. Preparation of 2,4,6-triiodo-N-methyl-3-(2,3,4,5,6-O-pentaacetylgluconamido)-5-(2,3,4,5,6-O-pentaacetylgluconyloxymethyl)-benzamide; III

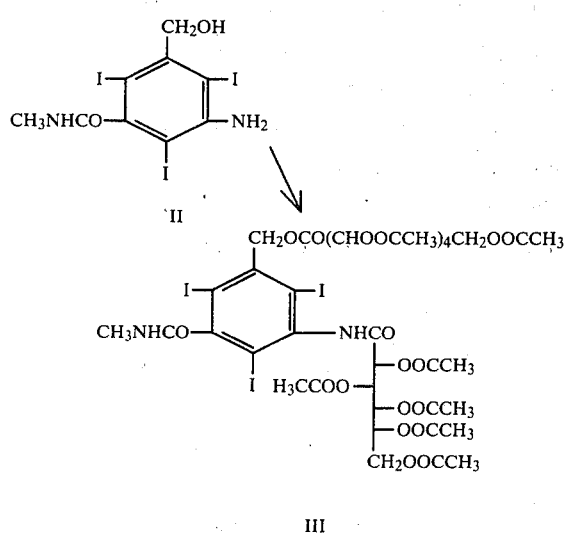

To 3-amino-5-hydroxymethyl-2,4,6-triiodo-N-methylbenzamide (II; 5.58 g., 0.01 mole) dissolved in dimethylacetamide (30 ml.) was added in one portion 2,3,4,5,6-O-pentaacetylgluconyl chloride (10.6 g.; 0.025 mole). After five days at room temperature, another 2.12 g. (0.005 mole) of 2,3,4,5,6-O-pentaacetylgluconyl chloride was added and stirring was continued at room temperature for another five days. The reaction mixture was then poured into water (25 ml.) and the mixture was stirred for 45 min. The aqueous solution was extracted with chloroform (3×25 ml.); the combined extracts were washed with 5% aqueous sodium bicarbonate (50 ml.), dried over sodium sulfate and evaporated in vacuo to give 13.35 g. (100%) of a colorless foam. The identity of the product was confirmed by nuclear magnetic resonance spectroscopy. The product was hydrolyzed without further purification.

3. Preparation of 3-D-gluconamido-5-hydroxymethyl-2,4,6-triiodo-N-methylbenzamide; IV

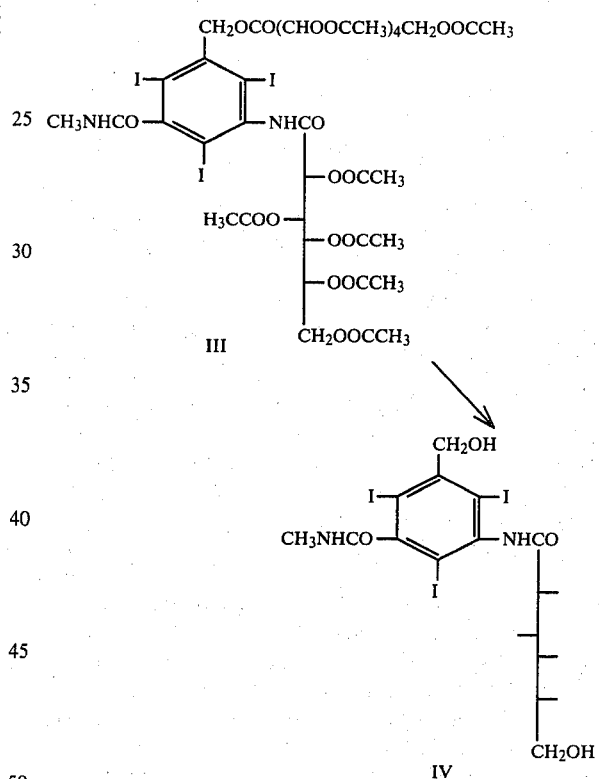

To 2,4,6-triiodo-N-methyl-3-(2,3,4,5,6-O-pentaacetylgluconamido)-5-(2,3,4,5,6-O-pentaacetylgluconyloxymethyl)-benzamide (III; 12.77 g.; 0.0096 mole) suspended in 60 ml. of a 1:1 methanol-water mixture was added sodium carbonate (5.58 g.; 0.053 mole). After 1.8 hr., 6.3 g. (0.106 mole) of glacial acetic acid as a 25% solution in water was added; and the mixture was concentrated under reduced pressure. The residue was taken up in water (160 ml.) and the pH was adjusted to 7 with dilute sodium hydroxide. After sitting overnight, the pH of the solution had dropped to 5.75 and more base was added to raise the pH to 7. The aqueous solution was extracted with 90% aqueous phenol (4×25 ml.). The combined phenolic extracts were washed with water (4×25 ml; a few drops of dilute hydrochloric acid were added to break up an emulsion that formed in the last wash) diluted with ether (300 ml.), and extracted with water (4×25 ml.). The combined, aqueous extracts were washed with 3:1 chloroform-isopropyl alcohol (6×100 ml. and 1×200 ml., contact time 30 min.), and then evaporated in vacuo resulting in 4.31 g. (58.5%) of a colorless, foam-like solid. Recrystallization from methanol followed by dissolving the product in water and evaporating the solution under reduced pressure gave analytically pure material, m.p. 234°–239° C. (dec.). The product was homogeneous by thin-layer chromatography (chloroform-methanol-acetic acid, 70:30:2). Its water solubility was determined to be 1.86% (w/v). The infrared and nuclear magnetic resonance spectra were consistent with the assigned structure.

Calc. for $C_{15}H_{19}I_3N_2O_8$: C, 24.47; H, 2.60; I, 51.73; N, 3.81. Found: C, 24.40; H, 2.73; I, 51.41; N, 3.73.

EXAMPLE VIII

3-Gluconamido-5-[N-(2-hydroxyethyl)acetamido]-2,4,6-triiodo-N-methylbenzamide

1. Preparation of 3-amino-5-[N-(2-hydroxyethyl)acetamido]-2,4,6-triiodo-N-methylbenzamide; II

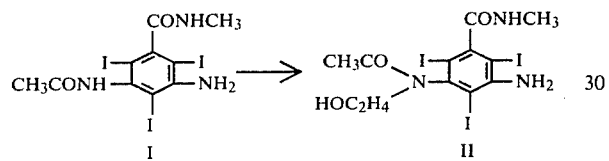

To a stirred solution of sodium ethoxide (prepared from 5.05 g. of sodium, 0.22 mole) in anhydrous ethanol (292.5 ml.) under nitrogen at 45° C., were added 3-acetamido-5-amino-2,4,6-triiodo-N-methylbenzamide (Example VI, compound III; 58.5 g.; 0.1 mole) and dimethylformamide (60 ml.).

The resulting dark, green, homogeneous solution was heated at 45°–50° C. for 0.75 hr. The solution was cooled to 10° C., and 2-chloroethanol (9.65 g., 0.12 mole) was added. The reaction mixture was then heated at 50° C. for 5 hours during which time a white precipitate formed. 2-Chloroethanol (4.025 g.; 0.05 mole) was added; the heterogeneous mixture was heated at 50° C. for 5.5 hr.; 2-chloroethanol (4.025 g.; 0.05 mole) was added and the mixture was heated at 50° C. for 5 hours and then was heated at 70° C. for 3 hours. After cooling overnight, the reaction mixture was filtered. The collected solid was washed with ethanol and then slurried in water (315 ml.) for 1.5 hr. The solid was collected and dried at 75° C. resulting in 52.36 g. (83%) of II. The product (1 g.) was taken up in hot methanol (50 ml.). The solution was filtered and boiled down to 10 ml. The solution was stored overnight at room temperature during which time analytically pure material crystallized, 0.55 g. (55% yield for the recrystallization). The infrared and nuclear magnetic resonance spectra were consistent with the assigned structure. The material melted at 265°–267° C. (dec.); the product was homogeneous by thin-layer chromatography (ethyl acetate-acetic acid; 98:2).

Calc. for $C_{12}H_{14}I_3N_3O_3$: C, 22.91; H, 2.24; I, 60.53; N, 6.68. Found: C, 22.91; H, 2.31; I, 60.29; N, 6.57.

2. Preparation of 2,4,6-triiodo-N-methyl-3-(2,3,4,5,6-O-pentaacetyl-gluconamido)-5-{N-[2-(2,3,4,5,6-O-pentaacetyl-gluconyloxy)ethyl]acetamido}benzamide; III

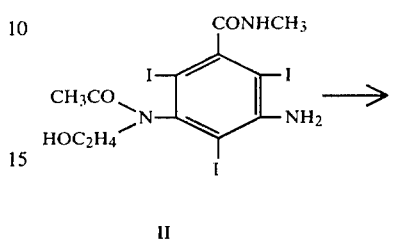

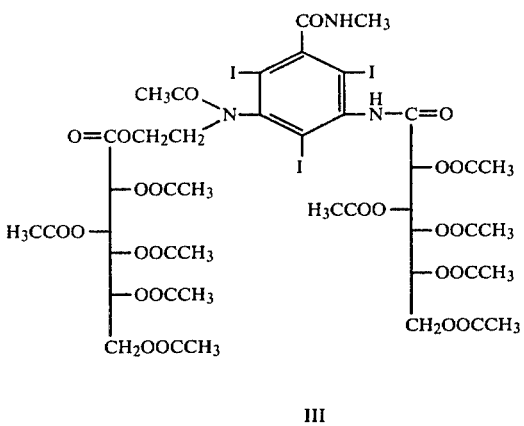

To a solution of 3-amino-5-[N-(2-hydroxyethyl)acetamido]-2,4,6-triiodo-N-methylbenzamide (II; 50.32 g.; 0.08 mole) dissolved in dimethylacetamide (252 ml.) was added in one portion 2,3,4,5,6-O-pentaacetylgluconyl chloride (101.88 g.; 0.24 mole; prepared by the method of C. E. Braun and C. D. Cook, Org. Syn., 41, 79 (1961)). After being stirred for six days at room temperature, the reaction mixture was poured into a mixture of dimethylacetamide (510 ml.) and water (680 ml.). The mixture was stirred for 2 hours, after which it was extracted with chloroform (3×340 ml.). The combined chloroform extracts were washed with 5% aqueous bicarbonate (2×340 ml.) and water (340 ml.), dried over sodium sulfate and evaporated under reduced pressure to give III as an oil, 132.75 g. (>100% due to the presence of dimethylacetamide as shown by the nuclear magnetic resonance spectrum). The product was homogeneous by thin-layer chromatography (ethyl acetate-acetic acid, 98:2), and the nuclear magnetic resonance spectrum was consistent with the assigned structure. The product was hydrolyzed without further purification.

3. Preparation of 3-gluconamido-5-[N-(2-hydroxyethyl)acetamido]-2,4,6-triiodo-N-methylbenzamide; IV

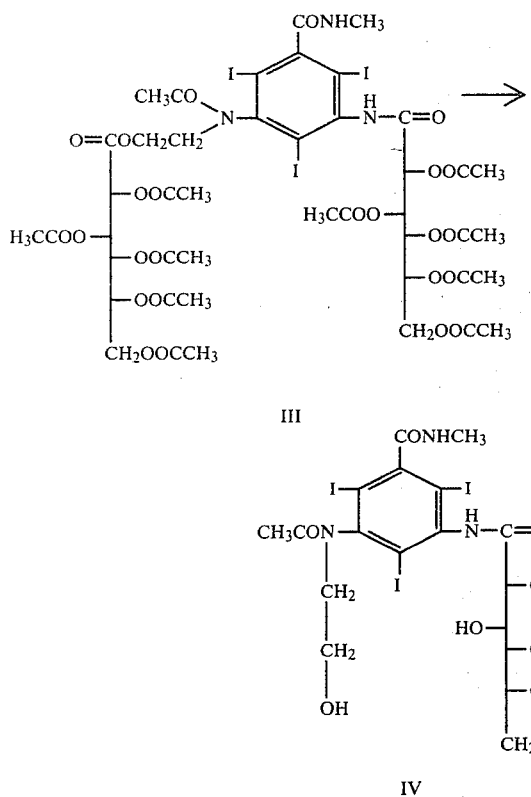

To 2,4,6-triiodo-N-methyl-3-(2,3,4,5,6-O-pentaacetyl-gluconamido)-5-{N-[2-(2,3,4,5,6-O-pentaacetyl-gluconyloxy)ethyl]acetamido}benzamide (III; 128.12 g. 0.08 moles based on the number of moles of starting material used to prepare III) suspended in 640 ml. of a 1:1 mixture of methanol and water was added in one portion sodium carbonate (53.34 g.; 0.503 mole). The heterogeneous reaction mixture was then stirred for 7 hours, after which time 60.39 g. (1.0 mole) of acetic acid (diluted with 120 ml. of water) was added. The mixture was filtered and then concentrated to 400 ml. under reduced pressure at 50° C. The mixture was adjusted to pH 7 with 50% sodium hydroxide and was stored at room temperature overnight during which time the pH did not change. The solution was extracted with 90% aqueous phenol (4×100 ml.). The combined phenolic extracts were washed with water (4×100 ml.; 20–60 drops of 10% hydrochloric acid were added each time to break up an emulsion), diluted with ether (1200 ml.) and extracted with water (4×100 ml.). The combined aqueous extracts were washed with a 3:1 mixture of chloroform and isopropyl alcohol (7×400 ml.; contact time 15–30 min.) and then was treated with charcoal (5 g.) overnight.

Due to the presence of two minor, higher $R_f$ impurities on thin-layer chromatography, the aqueous solution was taken to pH 10.25 with sodium carbonate, held there for 3 hours and 10 minutes, and then neutralized to pH 7 with concentrated hydrochloric acid followed by 10% hydrochloric acid. The aqueous solution was extracted with 90% phenol (1×150 ml., 3×50 ml.). The combined phenolic extracts were washed with water (4×50 ml.), diluted with ether (900 ml.) and extracted with water (4×50 ml.). The combined aqueous extracts were washed with a 3:1 mixture of chloroform and isopropyl alcohol (10×400 ml.; contact time 15–30 min.), treated with charcoal (3 g.) for 1.5 hours and then evaporated under reduced pressure (2 mm.) at 45° C. (water bath) to afford 31.76 g. (49%) of IV as a colorless foam; m.p. 153°–161° C.; thin-layer chromatography (chloroform-methanol-acetic acid, 70:30:2) showed two spots due to isomers. The infrared and nuclear magnetic resonance spectra were consistent with the assigned structure. The aqueous solubility is slightly less than 100%.

Calc. for $C_{18}H_{24}I_3N_3O_9$: C, 26.78; H, 3.00; I, 47.17; N, 5.21. Found: C, 26.46; H, 3.21; I, 47.50; N, 5.07.

Since a 5% solution of the above material had a pH of 8.45, the material was dissolved in water and the solution was adjusted to pH 5 with dilute hydrochloric acid and then to pH 7 with dilute sodium hydroxide. The solution was then carried through the phenol extraction procedure described above to give 23.38 g. (36.2%) of IV, m.p. 165°–174° C.; thin-layer chromatography results as above; pH of a 5% solution was 6.5.

EXAMPLE IX

3-Gluconamido-5-[N-(2-hydroxyethyl)acetamido]-2,4,6-triiodo-N-methylbenzamide

1. Preparation of 3-acetamido-5-amino-2,4,6-triiodo-N-methylbenzamide; II

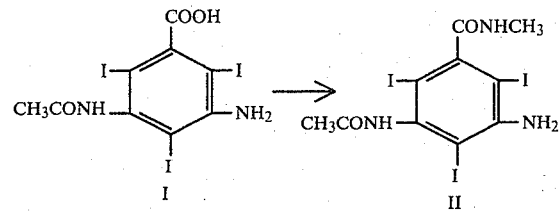

Dimethylacetamide (1710 ml.) and 3-acetamido-5-amino-2,4,6-triiodobenzoic acid (I, 572 g.; 1.0 mole) were placed in a 3-liter, 3-necked, round-bottomed flask equipped with a mechanical stirrer, addition funnel and thermometer. The contents were cooled to 0° C. (ice-ethanol bath) and thionyl chloride (159.5 ml.) was added to the stirred mixture at such a rate so as to maintain a temperature below 2° C. (required about 2 hrs.). The reaction mixture was allowed to warm to room temperature overnight.

The crude reaction mixture was added slowly over a period of about 40 minutes to 40% aqueous methylamine (1710 g.; 1928 ml.) at such a rate so as to maintain a temperature below 30° C. The resulting solution was allowed to evaporate in the air over the weekend and was concentrated under reduced pressure to a thick syrup. The syrup was poured into water (3 l.) and was stirred overnight to precipitate the desired product. The product was collected by suction filtration and dried overnight to provide 165.68 g. of the desired product in a crude yield of 28.3%. This material was only slightly contaminated by the starting acid and origin material [thin-layer chromatography, ethyl acetate-chloroform-acetic acid, 40:10:1].

If desired, the product may be purified in a yield of 20.6% by successive slurrying in hot methanol (4.8 ml./g.), in 3 N hydrochloric acid (10 ml./g., twice), in saturated sodium bicarbonate solution (12 ml./g., twice) and washing with distilled water.

2. The procedure of Example VIII, Paragraph No. 1, was followed to prepare 3-amino-5-[N-(2-hydroxyethyl)acetamido]-2,4,6-triiodo-N-methylbenzamide; III 3. Preparation of 2,4,6-triiodo-N-methyl-3-(2,3,4,5,6-O-pentaacetyl-gluconamido)-5-{N[2-(2,3,4,5,6-O-pentaacetyl-gluconyloxy)ethyl]acetamido}benzamide; IV

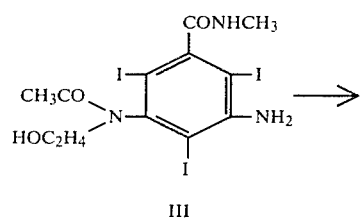

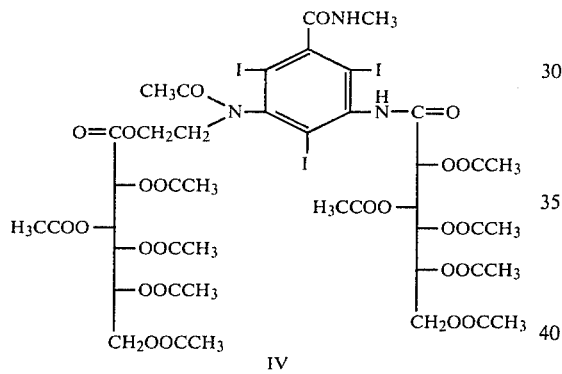

To a solution of 3-amino-5-[N-(2-hydroxyethyl)acetamido]-2,4,6-triiodo-N-methylbenzamide (III; 377.39 g.; 0.6 mole) in dimethylacetamide (1887 ml.) was added 2,3,4,5,6-O-pentaacetylgluconyl chloride (764.1 g.; 1.8 mole, prepared according to the method of C. E. Braun and C. D. Cook, *Org. Syn.*, 41, 79 (1961)). After stirring for five days at room temperature, the reaction mixture was diluted with water (3 l.) and dimethylacetamide (3 l.), was stirred for 2.5 hours and was extracted with chloroform (3×1 l.). The combined chloroform extracts were successively washed with a 5% solution of sodium bicarbonate (2×1.5 l., and 800 ml.) and water (1500 ml.) and dried over anhydrous sodium sulfate. The dried, organic extracts were concentrated under reduced pressure to provide an oily, foam-like residue (958.80 g.; 113.7%) which was sufficiently pure for use in the next step.

4. Preparation of 3-gluconamido-5-[N-(2-hydroxyethyl)]-2,4,6-triiodo-N-methylbenzamide; V

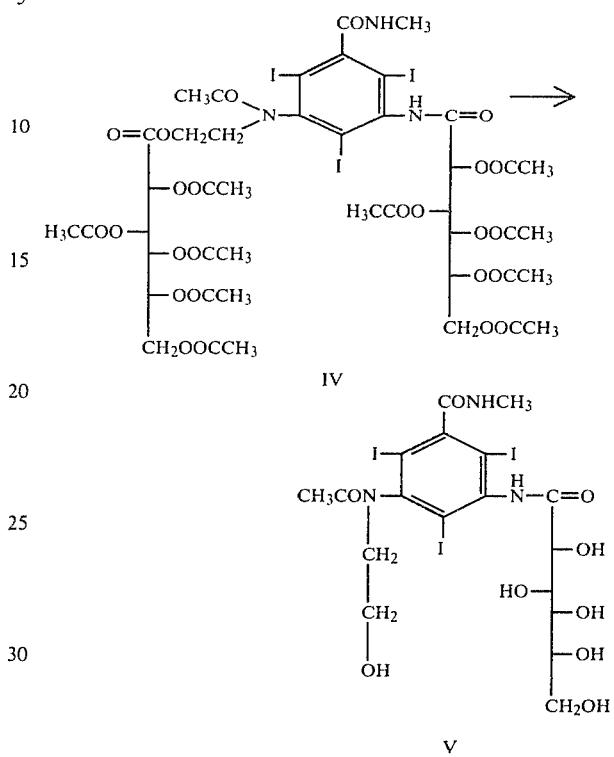

The product IV from Paragraph No. 3 above (958.8 g.; approximately 0.6 mole) was dissolved in methanol (2.3 l.) and water (2.3 l.) was added. Anhydrous sodium carbonate (349.77 g.; 3.3 mole) was added to the stirred suspension. After 3.5 hours of stirring, acetic acid (396.33 g. in 800 ml. of water) was added and solution effected. The reaction mixture was concentrated under reduced pressure to a volume of about 2500 ml. and 50% aqueous sodium hydroxide was added to pH 7. The solution was extracted with 90% phenol (4×250 ml.) and the phenolic extracts were washed with water (4×250 ml., diluted hydrochloric acid being added to break any emulsion formed). Ether (3 l.) was added to the combined phenolic extracts and the organic layer was extracted with water (4×250 ml.). The combined aqueous extracts were vigorously extracted with chloroform-isopropyl alcohol (3:1 and 7:3) solutions (53 extractions, total volume—37.8 l.) with intermittent treatment with decolorizing carbon (2×25 g.). After filtration through a 0.22 micron filter paper, the aqueous layer was concentrated and dried under reduced pressure to provide the desired product in an overall yield of 54.6% from the material produced in Paragraph No. 3 above. The product, m.p. 165°–174° C., was homogeneous by thin-layer chromatography (TLC) in two systems (chloroform-methanol-acetic acid, 70:30:2; chloroform-isopropyl alcohol, 24:16) showed two spots attributed to exo/endo isomers. TLC in a third system (chloroform-methanol-triethylamine, 26:12:2) showed a single spot. The elemental analysis and infrared spectrum are consistent with the assigned structure. The weight loss on drying is 1.54% (100° C., 0.05 mm., 1 hr.).

Calc. for $C_{18}H_{24}I_3N_3O_9$: C, 26.78; H, 3.00; I, 47.17; N, 5.21. Found: C, 26.76; H, 3.06; I, 46.97; 47.35; N, 5.19.

An additional quantity of material (about 4–5%) can be obtained from the chloroform-isopropyl alcohol extracts in the following manner. The chloroform-isopropyl alcohol washes are combined and extracted with water (1 l.). The aqueous extract is rewashed repeatedly with chloroform-isopropyl alcohol and is concentrated and dried under reduced pressure to provide the desired product. The aqueous solubility is slightly less than 100%.

EXAMPLE X

2-[N-(2-hydroxyethyl)acetamido]-2,4,6-triiodo-5-(2-keto-L-gulonamido)-N-methylbenzamide

1. Preparation of
3-(2,3:4,6-di-O-isopropylidene-2-keto-L-gulonamido)-5-{N-[2-(2,3:4,6-di-O-isopropylidene-2-keto-L-gulonyloxy)ethyl]acetamido}-2,4,6-triiodo-N-methylbenzamide: II

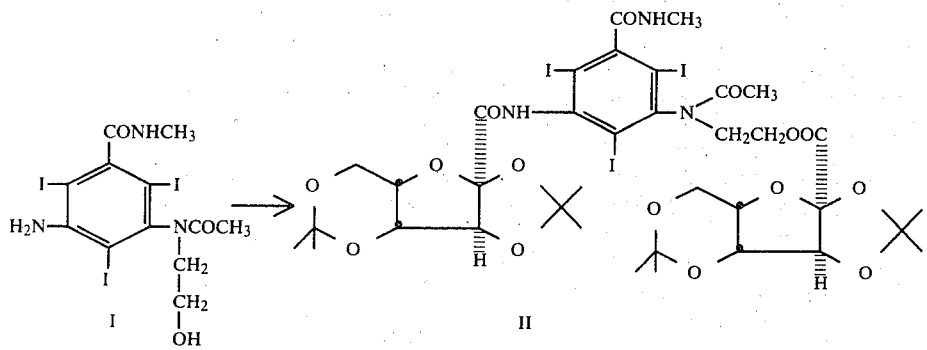

2,3:4,6-Di-O-isopropylidene-2-keto-L-gulonic acid monohydrate (Hoffmann-La Roche) was dried by azeotropic distillation with chloroform. A solution of the anhydrous sugar acid (122.2 g.; 0.445 mole) and dimethylacetamide (294 ml.) under a static nitrogen atmosphere was cooled to −10° C. (alcohol-ice bath). To the reaction mixture was added thionyl chloride (42.35 g.; 0.356 mole) at such a rate so as to maintain the temperature between −7° C. and −9° C. (about 1 hr. addition time). The reaction mixture was allowed to slowly warm to 10° C. over a 2.75 hr. period. To the reaction mixture was added 3-amino-5-[N-(2-hydroxyethyl)acetamido]-2,4,6-triiodo-N-methylbenzamide (I; 56 g.; 0.089 mole). The mixture was stirred for 2 days, after which it was slowly (over a 30–40 minute period) poured into an aqueous sodium bicarbonate slurry (99 g. in 1 l. of water). The mixture was then stirred for 20 minutes. Chloroform (300 ml.) was added and stirring was continued for 15 minutes. The layers were separated, and the aqueous layer was extracted with chloroform (2×300 ml.). The combined organic extracts were washed with 5% aqueous sodium bicarbonate (1 l.) and water (1 l.; 200 ml. of dimethylacetamide was added to break up an emulsion), dried over sodium sulfate and evaporated under reduced pressure to give II as an oil, 136.22 g. (>100% due to contamination by dimethylacetamide). Thin-layer chromatography (ethyl acetate-acetic acid: 98:2) showed two spots due to isomers. The product was used in the next step without further purification.

2. Preparation of
3-[N-(2-hydroxyethyl)acetamido]-2,4,6-triiodo-5-(2-keto-L-gulonamido)-N-methylbenzamide: III

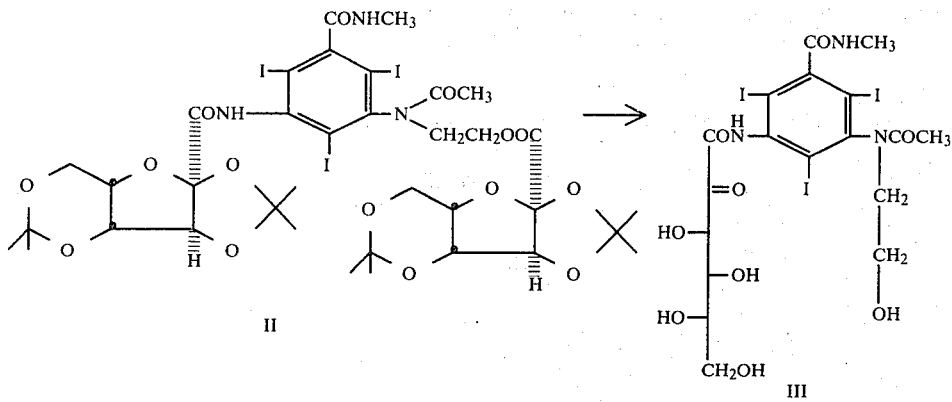

The crude product from step 1 (II; assume theory, i.e., 101.6 g.; 0.089 mole) was heated at reflux in a mixture of dioxane (1150 ml.) water (1915.6 ml.) and trifluoroacetic acid (19.16 ml.) for 10.75 hours. The reaction mixture was concentrated under reduced pressure to approximately 1500 ml. The pH of the mixture was adjusted to 7 with aqueous sodium hydroxide. The solution was extracted with 90% aqueous phenol (5×100 ml.). The combined phenol extracts were washed with water (2×100 ml.; 3×150 ml.), diluted with ether (1500 ml.) and extracted with water (3×150 ml.; 1×500 ml.). The combined aqueous layers were washed with a 3:1 mixture of chloroform-isopropyl alcohol (19×200 ml.; 3×300 ml.) with two intermittent overnight treatments with charcoal (7 g.). The aqueous solution was concentrated under reduced pressure to approximately 100 ml. The solution was filtered through a 0.22 micron filter pad and then was evaporated to dryness under reduced pressure to give III as a pale-yellow foam, 34.48 g. (48% from I), m.p. 197° C. (tan), 204°–220° C. (softens and darkens). Thin-layer chromatography (ethyl acetate-methanol-acetic acid: 80:20:2) showed two spots due to isomers. The solubility is initially 100% (w/v) dropping to 64% after 21 days. The infrared and nuclear magnetic resonance spectra were consistent with the assigned structure, and the infrared spectrum and thin-layer chromatogram were identical to those of the analytical sample.

The analytical data was obtained on a small sample prepared earlier; m.p. 185°–214° C. (dec.); thinlayer chromatography (ethyl acetate-methanol-acetic acid: 80:20:2) showed two spots due to isomers; the infrared and nuclear magnetic resonance spectra were consistent with the assigned structure; the solubility was initially 100% (w/v) but a precipitate formed after standing several days.

Calc. for $C_{18}H_{22}I_3N_3O_9$: C, 26.85; H, 2.75; I, 47.29; N, 5.22. Found: C, 27.07; H, 2.98; I, 47.31; N, 5.21.

EXAMPLE XI 3,5-Bis(D-Gluconamido)-2,4,6-Triiodo-N-Methylbenzamide

1. Preparation of 3,5-diamino-N-methylbenzamide monohydrochloride; II

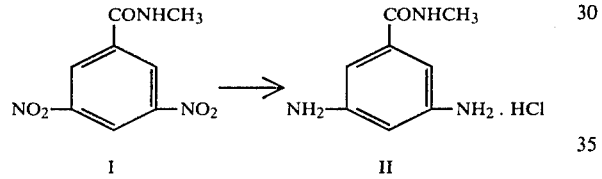

3,5-Dinitro-N-methylbenzamide (I; 45.04 g.; 0.2 mole;) was mixed with 5% Pd/C (6 g.). The reaction vessel was purged with argon, and methanol (500 ml.) was added. Reduction of the nitro groups was carried out at elevated pressures (10–43 psig) with a theoretical uptake of hydrogen (1.2 mole; 96 psig). The reaction mixture was filtered (to remove the catalyst) into a mixture of 10 ml. of concentrated hydrochloric acid and 40 ml. of water. The solution was concentrated to dryness in vacuo yielding 39.17 g. of 3,5-diamino-N-methylbenzamide monohydrochloride.

2. Preparation of 3,5-diamino-2,4,6-triiodo-N-methylbenzamide; III

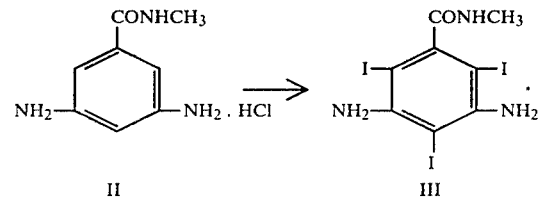

The crude product II from step 1 was dissolved in a mixture of 80 ml. of concentrated hydrochloric acid and 600 ml. of water. The system was placed under a nitrogen atmosphere, and the reaction mixture cooled to 0° C. Sodium iododichloride (260.4 ml. of a 2.42 N solution; 0.63 mole) was added dropwise in one hour while the temperature of the reaction mixture was held at 0°–5° C. The mixture was allowed to warm slowly to room temperature and stirred overnight. The precipitated solid was collected, slurried twice in 500 ml. portions of water for 10 minutes, and then in 500 ml. of methanol for 30 minutes. The solid was dried at room temperature in vacuo yielding 96.52 g. (89%) of 3,5-diamino-2,4,6-triiodo-N-methylbenzamide. Thin layer chromatography (ethyl acetate:chloroform:acetic acid; 40:10:1) showed one spot; the structure was confirmed by nmr and ir spectroscopy.

3. Preparation of 3,5-bis-(D-2,3,4,5,6-O-pentaacetylgluconamido)-2,4,6-triiodo-N-methylbenzamide; IV

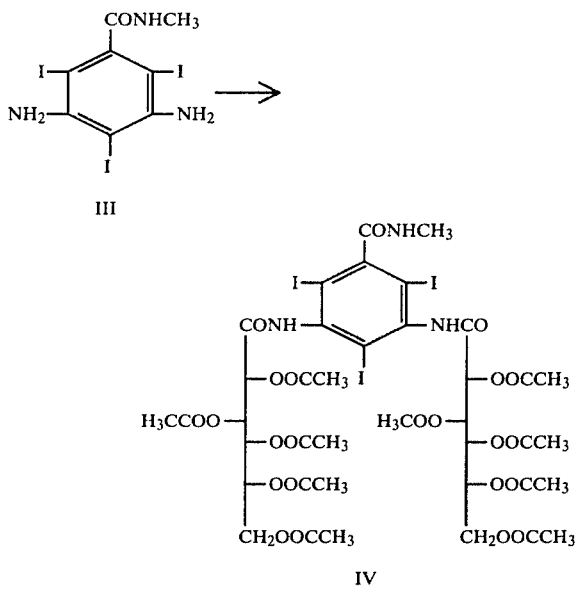

3,5-Diamino-2,4,6-triiodo-N-methylbenzamide (III; 81.45 g.; 0.15 mole) was dissolved in completely anhydrous dimethylacetamide (405 ml.). Under a nitrogen atmosphere, the reaction mixture was cooled to −24° C. 2,3,4,5,6-O-Pentaacetylgluconyl chloride [254.87 g.; 0.60 mole; prepared by the method of C. E. Braun and C. D. Cook, *Org. Syn.* 41, 79 (1961)] dissolved in dimethylacetamide (405 ml.) was added slowly in 70 min. while the temperature was held between −21° and −25° C. During a period of eight days the mixture was stirred for a total of about 48 hours. Most of the stirring was done at temperatures within the range of −15° to −24° C., although during a four-hour period near the end the temperature was within the range of −10° to −15° C. There were four overnight intervals and a weekend interval within this eight-day period during which the mixture was not stirred. During the first two overnight intervals, the mixture was frozen (using dry ice), followed by thawing the next morning to permit resumption of stirring. During the other intervals of non-stirring the homogeneous mixture was stored at about −30° C. At this point, thin layer chromatography (ethyl acetate:chloroform:acetic acid; 30:20:1) showed complete monoacylation; no starting material could be detected. Acylation was completed at room temperature with stirring. This was continued for six days, although thin layer chromatography indicated that diacylation was complete after one day.

The reaction mixture was poured into water (750 ml.), and the solution was stirred for 75 min. The aqueous solution was extracted with 3×375 ml. portions of chloroform. The combined chloroform extract was washed with 3×750 ml. portions of sodium bicarbonate solution (5%), then once with water (750 ml.). It was then dried over sodium sulfate, and evaporated in vacuo to give 236.84 g. of an oily product which contained some residual dimethylacetamide. Thin layer chromatography (ethyl acetate:chloroform:acetic acid; 30:20:1) indicated the material to be essentially pure with trace amounts of three impurities. The material was used in the next step without further purification.

4. Preparation of 3,5-bis-D-gluconamido-2,4,6-triiodo-N-methylbenzamide; V

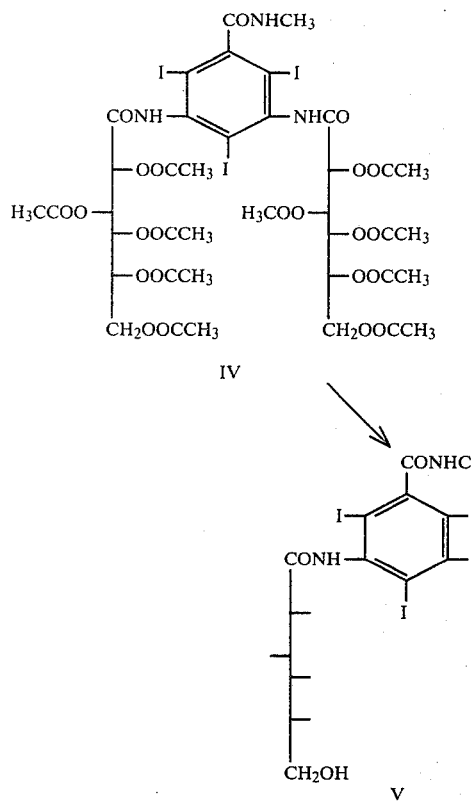

The crude product IV from step 3 was dissolved in a 1:1 mixture of methanol and water (2400 ml.); to this mixture was added sodium carbonate (94.96 g.; 0.896 mole) in one portion. After being stirred for 80 min. at room temperature, the reaction mixture was filtered, then neutralized with acetic acid (41.5 g.). The solution was passed through a column containing 5250 ml. (1.75 eq/ml.) of cation exchange resin [marketed under the trade designation "Amberlite IR-120 (H)" (Rohm & Haas Co., Philadelphia, Pa./Mallinckrodt, Inc., St. Louis, Mo.)]. The solution was then concentrated in vacuo to a volume of approximately 700 ml. and was then treated with charcoal (10 g.) overnight. The mixture was filtered and the filtrate was evaporated to dryness in vacuo to give 122.79 g. of crude product (91% crude yield). The crude product was recrystallized three times from methanol (ml./g. ratios: 15/1; 15/1; 20/1). Following each rectystallization, the damp cake was dissolved in water; the resulting aqueous solution was evaporated to dryness in vacuo. The recrystallization procedure yielded 70.5 g. (52%) of 3,5-bis-D-gluconamido-2,4,6-triiodo-N-methylbenzamide (V); thin layer chromatography (n-butyl alcohol:water:acetic acid; 100:75:30) indicated the compound was essentially pure, with trace amounts of two impurities; the aqueous solubility is initially 100% (w/v), dropping to <15% after 24 hr. The ir and nmr spectra were consistent with the assigned structure. M.P., 144°–148° C. (softens at 130° C.).

Calcd. for $C_{20}H_{28}I_3N_3O_{13}$: C, 26.71; H, 3.14; I, 42.34; N, 4.67. Found: C, 26.73; H, 3.48; I, 42.34; N, 4.75.

EXAMPLE XII 3,5-Bis-(D-Gluconamido)-2,4,6-Triiodo-N-Methylbenzamide

1. Preparation of 3,5-bis-(D-2,3,4,5,6-O-pentaacetylgluconamido)-2,4,6-triiodo-N-methylbenzamide; II

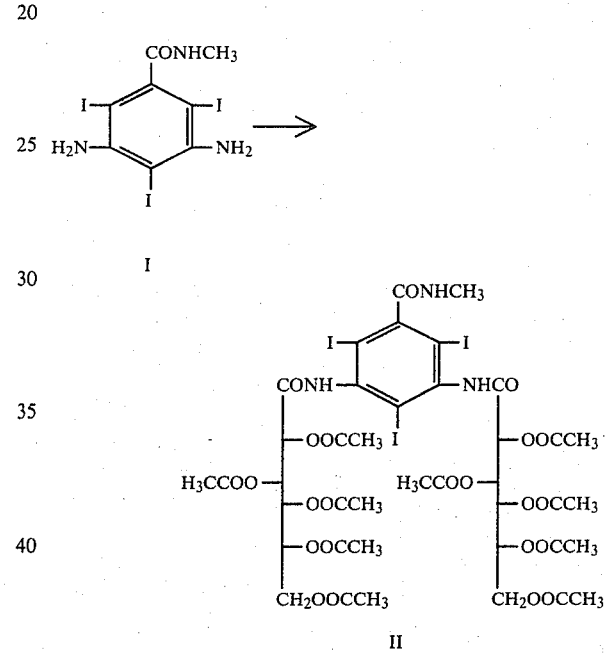

In a 12-l-3-neck flask were placed anhydrous dimethylacetamide (7440 ml.; dried over molecular Sieves) and 3,5-diamino-2,4,6-triiodo-N-methylbenzamide (I; 507.6 g.). The solution was protected with a Drierite tube and cooled in a mixture of ice: 2-propanol to a temperature of −5° C. 2,3,4,5,6-O-Pentaacetylgluconyl chloride was added at once and the mixture was stirred in the ice: 2-propanol mixture at −5° C. to −1° C. in a refrigerator. Thin layer chromatography (ethyl acetate:acetic acid; 49:1) after 72 hours showed no starting material. The mixture was then stirred at room temperature for 2 days; thin layer chromatography in the same manner showed complete reaction. The mixture was stirred for one hour with distilled water (7 l.) and extracted with chloroform (14×500 ml.). The extract was washed with 10% sodium bicarbonate solution (6×500 ml.), then with water (3×800 ml.) and finally dried over sodium sulfate, filtered and the filtrate was evaporated to dryness to obtain 2010 g. (above 100% due to dimethylacetamide) of a brown semisolid material.

2. Preparation of 3,5-bis-(D-gluconamido)-2,4,6-triiodo-N-methylbenzamide; III

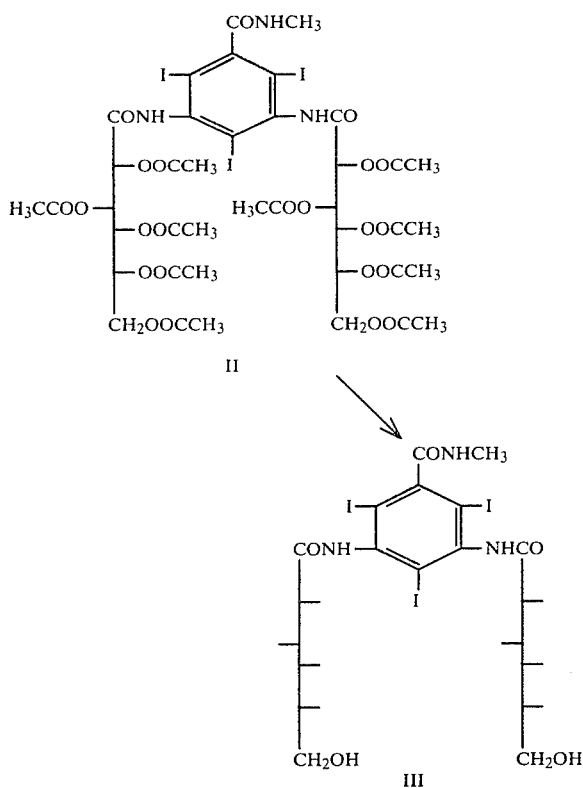

A solution of 3,5-bis-(D-2,3,4,5,6-O-pentaacetyl-gluconamido)-2,4,6-triiodo-N-methylbenzamide (II) in methanol (3500 ml.) was treated with a solution of sodium carbonate (495.4 g., 4.67 mol.) in distilled water (3500 ml.) The mixture was stirred at room temperature for a total of 60 minutes. The reaction was followed by thin layer chromatography (ethyl acetate:acetic acid; 49:1) and was complete within one hour. The mixture was treated with glacial acetic acid (240 ml.) to obtain a pH of 7.

The solution was divided into two equal portions. Each portion was passed through a column containing 14 lbs. (about 3 equivalent of resin) of cation exchange resin ("Amberlite IR-120 (H)"; Rohm & Haas Co., Philadelphia, Pa.) previously washed to colorless with a 1:1 methanol:water mixture. Each column was eluted with a total of a 1:1 methanol:water mixture (21–27 l.). The combined eluates (pH 3.3) were concentrated to 2.5 l.; and the concentrate was stirred overnight at room temperature with charcoal (50 g.; "Darco G-60"). The mixture was evaporated to dryness at 45°–50° C., and the brown gummy residue obtained was boiled with a portion of methanol (total of 4 l.). The clear solution was allowed to crystallize overnight at room temperature to obtain pale yellow crystals. The crystals were filtered, washed with methanol and dissolved in distilled water (1.5 l.). The solution was evaporated to dryness to obtain a gummy residue. The residue was dissolved in water (650 ml.) by heating on a steam bath and concentrated in vacuo to obtain a thick syrup which was poured onto a stirred volume of methanol (7.5 l.) at 64° C. The clear yellow solution became turbid within minutes. The mixture was stirred at room temperature for two hours and the crystals obtained were filtered, washed with methanol, dissolved in water (2 l.) and stirred overnight at room temperature with charcoal (30 g.).

The mixture was filtered, evaporated to dryness, and the residue was dissolved with heat on a steam bath in water (30 ml.) and poured with stirring into methanol (7.5 l.) at 64° C. After standing overnight at room temperature, the crystals were filtered, washed with methanol and then with ether. Thin layer chromatography and liquid chromatography indicated the material to be essentially pure with traces of two impurities. The material was dissolved in water (840 ml.), stirred overnight at room temperature with charcoal (20 g.) and filtered. The combined filtrate was concentrated to a small volume, passed through a Millipore filter (0.2μ), evaporated to dryness and dried for 3.5 days over phosphorous pentoxide at 0.5 mm. Hg. to obtain pale white amorphous material (286 g.). Thin layer chromatography developed in butyl alcohol:acetic acid:water; 10:5:2 and 100:75:30 indicated the material to be essentially pure with traces of two impurities and showed no gluconic acid when plate sprayed with 5% sulfuric acid in methanol and dried; m.p. softened at 118°–128° C. with total melt at 140°–152° C. The ir and nmr spectra were consistent with the assigned structure. The pH of a 5% solution was 4.5.

| Elemental analysis: $C_{20}H_{28}I_3N_3O_{13}$ With drying | C | H | I | N |
| --- | --- | --- | --- | --- |
| Calc. % | 26.71 | 3.14 | 42.34 | 4.67 |
| Found % | 26.83 | 3.43 | 41.26 | 4.40 |
|  |  |  | 41.01 |  |

A 15% w/v solution was prepared, seeded and stirred at room temperature. A turbidity developed within two hours. The solution was filtered through a Millipore filter, and an aliquot from the filtrate was evaporated to constant weight in an oven at 85° C. to obtain a solubility of 12%.

Toxicity evaluations in accordance with three different techniques were carried out on aqueous solutions of the compounds of Examples I, II, IV, V, VI, VIII, IX, X, XI and XII. The techniques utilized are described below.

1. Acute Intravenous Toxicity Studies in Mice

Except as noted below, Swiss Albino mice (Charles River) were dosed in the lateral tail vein with solutions of the above-noted iodinated compounds having an iodine concentration of 28.2% with a pH of 7.0–7.2. The solutions were injected at the rate of approximately 1 ml./min. In the case of the compound of Examples I, II and VI, supersaturated solutions having an iodine concentration of 10%, 28% and 28%, respectively, were employed. Following injections, the animals were observed for immediate reactions and then daily throughout a seven-day observation period. The $LD_{50}$ values were calculated by the method of Litchfield and Wilcoxon (*J. of Pharmac.* and *Exptl. Therap.* 96:99–113, 1949).

2. Intracerebral Toxicity in Mice

Swiss Albino mice (Charles River) were used. Fixed volumes of aqueous solutions of the iodinated compounds were injected intracerebrally via a 27-gauge needle (¼ inch in length) according to the method of Haley et al. (*Br. J. of Pharmac.* 12:12–15, 1957). Again in the case of the compounds of Examples I, II and VI, supersaturated solutions were employed. In the case of the compound of Examples VIII and IX, solutions having an iodine concentration of 35% and 42%, respectively, were employed and in the case of the compound of Example X, a solution having an iodine concentration of 40% was employed. The animals were observed immediately following injections and daily throughout a seven day observation period. The LD$_{50}$ values were calculated by the method of Litchfield and Wilcoxon (*J. of Pharmac. and Exptl. Therap.* 96:99–113, 1949).

3. Intracisternal Toxicity in Rats

Sprague-Dawley (Carworth) rats were used. The method used was a variation of the procedure outlined by Melartin et al. (*Invest. Rad.* 5:13–21, 1970). In the case of the compound of Examples VIII and IX, solutions having an iodine concentration of 35% and 40%, respectively, were employed and in the case of the compound of Example X, a solution having an iodine concentration of 40% was employed. After dosing, the animals were housed individually and observed for immediate reactions and periodically for a two day observation period. The LD$_{50}$ values were calculated according to the method of Litchfield and Wilcoxon (*J. of Pharmac. and. Exptl. Therap.* 96:99–115, 1949).

The results of these toxicity evaluations made on solutions of five compounds of the invention are set forth in Table 1.

TABLE 1

Toxicity Values of Compounds of the Invention

| Compound | LD$_{50}$ Value (mg. I/kg. body wt.) | | |
|---|---|---|---|
| | I.V. (Mice) | Intra-cerebral (Mice) | Intra-cisternal (Rats) |
| Example I | >10,000 | >750 | >150 |
| Example II | 8,085 | 2,350 | 100 |
| Example IV | 6,400 | 1,175 | 75 |
| Example V | 1,700 | 1,700 | 28 |
| Example VI | 11,000 | ~2,000 | 180 |
| Examples VIII and IX (Iodine Conc.) | | | |
| 28.2% | >13,000 | | |
| 40% | 14,500 | | |
| 35% | | >2,679 | |
| 42% | | 2,200 | |
| 35% | | | >505 |
| 40% | | | 590 |
| Example X (Iodine Conc.) | | | |
| 28.2% | ~10,500 | | |
| 40% | | 2,500 | 405 |
| Examples XI and XII | 20,500 | 1,330 | >560 |

The compound of Example I was tested as a bronchographic agent in a dog with good results. The compound of Example II was employed in intravenous pyelographic studies carried out in dogs. At a dosage of 250 mg. I/kg., kidney shadows were observed one minute after injection and the ureters and urinary bladder were visible five minutes after injection. At a dosage of 350 mg. I/kd., the compound of Example IV gave a shadow of the urinary bladder 40 minutes after injection into a dog. At a dosage of 350 mg. I/kg., the compound of Example V gave a kidney shadow with partial visualization of the ureters 5 minutes after injection into a dog. At a dosage of 190 mg. I/kg., the compound of Example VI gave a kidney shadow with partial visualization of the ureters one minute after injection into a dog. The compound of Examples VIII and IX was employed in intrathecal myelographic studies carried out in dogs. At dosages of 282 to 2400 mg. I/kg., it was observed that there was good filling of the subarachnoid space from the cul-de-sac to the thoracic, cervical and cisterna magna depending on the volume injected and the size of the test animal. The compound of Examples VIII and IX was employed in intracisternal toxicity studies carried out in dogs using the cisterna magna as the route of administration. At a dosage of 1410 mg. I/kg., it was observed that there was a partial filling of the cerebral subarachnoid space and good cervical and thoracic subarachnoid space filling. The compound of Example X was employed in intravenous pyelographic studies carried out in rats. At a dosage of 500 mg. I/kg., faint kidney and portions of ureters were observed five minutes after injection. At 10 minutes, the collecting pelvis of the right kidney showed good filling. The urinary bladder showed good contrast at 10 and 15 minutes after dosing. At a dosage of 70 mg. I/kg. of the compound of Examples XI and XII administered by intrathecal injection into dogs, the radiographs obtained revealed fair filling with some degree of scalloping. In a separate study, the compound of Examples XI and XII was administered to dogs by intraspinal administration at a dosage of 70 mg. I/kg. The radiographs obtained revealed that the lumbar and sacral spinal spaces were well defined.

As will be apparent to those skilled in the art, other compounds such as 5-gluconamido-N-(2-hydroxyethyl)-2,4,6-triiodo-N,N'-dimethylisophthalamide within the scope of the invention in addition to those specifically disclosed in the above examples may be prepared by the same general methods.

In view of the above, it will be seen that the several objects of the invention are achieved and other advantageous results attained.

As various changes could be made in the above methods and products without departing from the scope of the invention, it is intended that all matter contained in the above description shall be interpreted as illustrative and not in a limiting sense.

What is claimed is:

1. A compound of the formula:

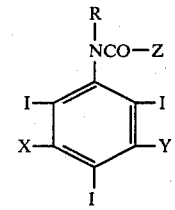

wherein X and Y are each non-ionizing functions compatible with water solubility and/or low toxicity in the 2,4,6-triiodophenyl configuration, R is selected from the group consisting of hydrogen, lower alkyl and hydroxy-lower alkyl and CO—Z is the acyl residue of a polyhydroxy-monobasic acid, said acyl residue containing not more than 8 carbon atoms in its chain or ring.

2. A compound as set forth in claim 1 wherein CO—Z is the acyl residue of a polyhydroxy-monobasic acid selected from the group consisting of aldonic acids, branched chain polyhydroxy-alkanoic acids, uronic acids, deoxy-aldonic acids, acylamino-deoxy-aldonic acids and polyhydroxy-cycloalkane carboxylic acids.

3. A compound as set forth in claim 1 wherein X and Y are each selected from the group consisting of lower alkoxy, hydroxy-(lower alkoxy), lower alkoxy-(lower alkoxy), lower acylamino, lower acylamino-(lower alkyl), lower acylamino(lower acylamino), hydroxy-lower acylamino, N-(hydroxy lower alkyl)-lower acylamino, N-(lower alkyl)-lower acylamino, lower alkylsulfonamido, N-(lower alkyl)-lower alkylsulfonamido, 3,3-bis-(lower alkyl)-ureido, lower perfluoroacylamino, carbamyl, N-(lower alkyl)carbamyl, N,N-di-(lower alkyl)carbamyl, N-(hydroxy lower alkyl)carbamyl, N-(hydroxy lower alkyl)-N-(lower alkyl)carbamyl, lower alkoxy-(lower acylamino), lower alkoxy-alkoxy-(lower acylamino), hydroxy and hydroxy-lower alkyl functions.

4. A compound as set forth in claim 1 wherein one of X and Y is selected from the group consisting of hydrogen lower alkoxy, hydroxy-(lower alkoxy), lower alkoxy-(lower alkoxy), lower acylamino, lower acylamino-(lower alkyl), lower acylamino (lower acylamino), hydroxy-lower acylamino, N-(hydroxy lower alkyl)-lower acylamino, N-(lower alkyl)-lower acylamino, lower alkylsulfonamido, N-(lower alkyl)-lower alkylsulfonamido, 3,3-bis-(lower alkyl)-ureido, lower perfluoroacylamino, carbamyl, N-(lower alkyl)carbamyl, N,N-di-(lower alkyl) carbamyl, N-(hydroxy lower alkyl)carbamyl, N-(hydroxy lower alkyl)-N-(lower alkyl)carbamyl, lower alkoxy-(lower acylamino), lower alkoxy-alkoxy-(lower acylamino), hydroxy and hydroxy-lower alkyl functions and the other of X and Y is

where R is selected from the group consisting of hydrogen, lower alkyl and hydroxy-lower alkyl and CO-Z is the acyl residue of a polyhydroxy-monobasic acid selected from the group consisting of aldonic acids, branched chain polyhydroxyalkanoic acids, uronic acids, deoxy-aldonic acids, acylamino-deoxy-aldonic acids and polyhydroxy-cycloalkane carboxylic acids.

5. A compound as set forth in claim 2 wherein CO-Z is the acyl residue of a polyhydroxy-monobasic acid selected from the group consisting of aldonic acids and uronic acids.

6. A compound as set forth in claim 3 wherein X and Y are each selected from the group consisting of lower acylamino, N-(hydroxy lower alkyl)-lower acylamino, N-(lower alkyl)-lower acylamino, carbamyl, N-(lower alkyl)carbamyl and N,N-di-(lower alkyl)carbamyl.

7. A compound as set forth in claim 1 wherein X is an N-[hydroxy-(lower alkyl)]lower acylamino function.

8. A compound as set forth in claim 7 wherein X is N-(2-hydroxyethyl)acetamido.

9. A compound as set forth in claim 1 wherein X and Y are each N-methylcarbamyl, R is hydrogen and CO-Z is the acyl residue of gluconic acid.

10. A compound as set forth in claim 1 wherein X is N-methylcarbamyl, Y is N,N-dimethylcarbamyl, R is hydrogen and CO-Z is the acyl residue of gluconic acid.

11. A compound as set forth in claim 1 wherein X is N-methylcarbamyl, Y is N,N-dimethylcarbamyl, R is hydrogen and CO-Z is the acyl residue of 2-deoxy-2-oxogulonic acid.

12. A compound as set forth in claim 1 wherein X is N-methylcarbamyl, Y is N-methylacetamido, R is hydrogen and CO-Z is the acyl residue of gluconic acid.

13. A compound as set forth in claim 1 wherein X is N-methylcarbamyl, Y is N,N-dimethylcarbamyl, R is methyl and CO-Z is the acyl residue of galacturonic acid.

14. A compound as set forth in claim 1 wherein X is N-methylcarbamyl, Y is acetamido, R is hydrogen and CO-Z is the acyl residue of gluconic acid.

15. A compound as set forth in claim 1 wherein X is N-methylcarbamyl, Y is hydroxymethyl, R is hydrogen and CO-Z is the acyl residue of gluconic acid.

16. A compound as set forth in claim 1 wherein X is N-(2-hydroxyethyl)acetamido, Y is N-methylcarbamyl, R is hydrogen and CO-Z is the acyl residue of gluconic acid.

17. A compound as set forth in claim 1 wherein X is N-(2-hydroxyethyl)acetamido, Y is N-methylcarbamyl, R is hydrogen and CO-Z is the acyl residue of 2-deoxy-2-oxogulonic acid.

18. A compound as set forth in claim 1 where X is N-methylcarbamyl, Y is gluconamido, R is hydrogen and CO-Z is the acyl residue of gluconic acid.

* * * * *